(12) United States Patent
Gordon et al.

(10) Patent No.: US 12,173,041 B2
(45) Date of Patent: *Dec. 24, 2024

(54) CYCLIN G1 INHIBITORS AND RELATED METHODS OF TREATING CANCER

(71) Applicant: DELTA NEXT-GENE, LLC, Santa Monica, CA (US)

(72) Inventors: Erlinda M. Gordon, Santa Monica, CA (US); Frederick L. Hall, Santa Monica, CA (US)

(73) Assignee: Delta Next-Gene, LLC, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/713,809

(22) Filed: Apr. 5, 2022

(65) Prior Publication Data

US 2022/0380802 A1 Dec. 1, 2022

Related U.S. Application Data

(63) Continuation of application No. 16/483,308, filed as application No. PCT/US2018/016643 on Feb. 2, 2018, now Pat. No. 11,325,958.

(60) Provisional application No. 62/533,595, filed on Jul. 17, 2017, provisional application No. 62/454,775, filed on Feb. 4, 2017.

(51) Int. Cl.
| | |
|---|---|
| *C07K 14/47* | (2006.01) |
| *A61K 38/17* | (2006.01) |
| *A61K 47/69* | (2017.01) |
| *C07K 7/06* | (2006.01) |
| *C12N 9/12* | (2006.01) |
| *C12N 15/86* | (2006.01) |
| *G01N 33/574* | (2006.01) |
| *G01N 33/68* | (2006.01) |
| *A61K 38/00* | (2006.01) |
| *A61K 48/00* | (2006.01) |

(52) U.S. Cl.
CPC .......... *C07K 14/4738* (2013.01); *A61K 38/17* (2013.01); *A61K 47/6901* (2017.08); *C07K 7/06* (2013.01); *C12N 9/1211* (2013.01); *C12N 15/86* (2013.01); *G01N 33/574* (2013.01); *G01N 33/6818* (2013.01); *G01N 33/6848* (2013.01); *A61K 38/00* (2013.01); *A61K 48/00* (2013.01); *C12N 2740/13043* (2013.01); *C12Y 207/01021* (2013.01); *G01N 2333/4739* (2013.01)

(58) Field of Classification Search
CPC .. C07K 14/4738; C12N 15/86; C12N 9/1211; A61P 35/00; G01N 33/574; C12Y 207/01021
See application file for complete search history.

(56) References Cited

U.S. PATENT DOCUMENTS

| | | | | |
|---|---|---|---|---|
| 6,825,033 | B2* | 11/2004 | Gordon | A61K 38/1709 |
| | | | | 435/320.1 |
| 7,605,142 | B2* | 10/2009 | Gordon | C07K 14/4738 |
| | | | | 514/44 R |
| 7,708,986 | B2* | 5/2010 | Gordon | A61K 38/193 |
| | | | | 514/44 R |
| 11,325,958 | B2* | 5/2022 | Gordon | A61K 38/17 |
| 2002/0035079 | A1 | 3/2002 | Gordon et al. | |
| 2003/0086927 | A1* | 5/2003 | Gordon | C07K 16/18 |
| | | | | 424/155.1 |
| 2004/0138419 | A1 | 7/2004 | Zahner | |
| 2007/0172486 | A1 | 7/2007 | Gordon et al. | |
| 2010/0016413 | A1* | 1/2010 | Hall | A61P 1/04 |
| | | | | 435/320.1 |
| 2012/0027727 | A1 | 2/2012 | Hall et al. | |
| 2012/0040376 | A1 | 2/2012 | Ueda et al. | |
| 2016/0011198 | A1 | 1/2016 | Dittamore | |
| 2016/0355887 | A1 | 12/2016 | Watson et al. | |

FOREIGN PATENT DOCUMENTS

| | | |
|---|---|---|
| JP | 5892666 B2 | 3/2016 |
| WO | 2018144863 A1 | 8/2018 |

OTHER PUBLICATIONS

Chawla et al. "Three year results of Blessed: Expanded access for DeltaRex-G for an intermediate size population with advanced pancreatic cancer and sarcoma (NCT04091295) and individual patient use of DeltaRex-G for solid malignancies (IND#19130) ", 2022, 10 pages (Year: 2022).*

Gordon et al. "Targeting metastatic cancer from the inside: A new generation of targeted gene delivery vectors enables personalized cancer vaccination in situ", International Journal of Oncology, 665-675, 2008 (Year: 2008).*

(Continued)

*Primary Examiner* — Lianko G Garyu

(74) *Attorney, Agent, or Firm* — Hartmans Law Group; Joel Fogelson

(57) ABSTRACT

Methods of treating a cancer in a patient are provided. The methods can include obtaining a tumor sample from a patient, detecting whether CCNG1 gene expression is present in the tumor sample, diagnosing the patient with a CCNG1 inhibitor-responsive cancer when the presence of CCNG1 gene expression in the tumor sample is detected, and/or administering an effective amount of a CCNG1 inhibitor to the diagnosed patient. CCNG1 inhibitors can include a viral vector having a binding peptide that is configured to bind one or more signature (SIG) elements of an invading tumor and at least one cytocidal gene. CCNG1 inhibitors including cell penetrating peptides are also provided.

12 Claims, 8 Drawing Sheets

Specification includes a Sequence Listing.

(56) References Cited

OTHER PUBLICATIONS

Lenz et al. "Tumor Site Specific Phase I Evaluation of Safety and Efficacy of Hepatic Arterial Infusion of a Matrix-Targeted Retroviral Vector Bearing a Dominant Negative Cyclin G1 Construct as Intervention for Colorectal Carcinoma Metastatic to Live", Human Gene Therapy, 2002, 1515-1537 (Year: 2002).*

International Search Report and Written Opinion for PCT/US2018/016643 issued on May 14, 2018, 14 pages.

International Preliminary Report on Patentability for PCT/US2018/016643 issued on Aug. 6, 2019, 12 pages.

Rahib, L., et al., "Projecting Cancer Incidence and Deaths to 2030: The Unexpected Burden of Thyroid, Liver, and Pancreas Cancers in the United States", Cancer Research, pp. 1-11 (May 2014).

"Cancer facts & figures 2018", American Cancer Society, pp. 1-76 (2018).

Conroy, T., et al., "FOLFIRINOX versus Gemcitabine for Metastatic Pancreatic Cancer", The New England Journal of Medicine, vol. 364, No. 19, pp. 1817-1825 (May 12, 2011).

Von Hof, D.D., et al., "Increased Survival in Pancreatic Cancer with nab-Paclitaxel plus Gemcitabine", The New England Journal of Medicine, vol. 369, No. 18, pp. 1691-1703 (Oct. 31, 2013).

Wang-Gillam, A., et al., "Nanoliposomal irinotecan with fluorouracil and folinic acid in metastatic pancreatic cancer after previous gemcitabine-based therapy (NAPOLI-1): a global, randomised, open-label, phase 3 trial", The Lancet, vol. 387, No. 10018, pp. 545-557 (Feb. 6-12, 2016) (Abstract).

Moore, J. M., et al., "Erlotinib Plus Gemcitabine Compared With Gemcitabine Alone in Patients With Advanced Pancreatic Cancer: A Phase III Trial of the National Cancer Institute of Canada Clinical Trials Group", Journal of Clinical Oncology, vol. 25, No. 15, pp. 1960-1966 (May 20, 2007).

Liu, L., et al., "Primers on Molecular Pathways—Cycling toward Pancreatic Cancer", Pancreatology, vol. 10, No. 1, pp. 6-13 (Mar. 2010).

Matera, R., and Saif, M.W., "New therapeutic directions for advanced pancreatic cancer: cell cycle inhibitors, stromal modifiers and conjugated therapies", Expert Opinion on Emerging Drugs, vol. 2, No. 3, pp. 223-233 (2017) (Abstract).

Waehler, R., "Engineering targeted viral vectors for gene therapy", Nature Reviews Genetics, vol. 8, pp. 573-587 (Aug. 2007).

Hall, F.L., et al., "Molecular Engineering of Matrix-Targeted Retroviral Vectors Incorporating a Surveillance Function Inherent in von Willebrand Factor", Human Gene Therapy, vol. 11, No. 7, pp. 983-993 (2000).

Xu, F., et al., "Long term inhibition of neointima formation in balloon-injured rat arteries by intraluminal instillation of a matrix-targeted retroviral vector bearing a cytocidal mutant cyclin G1 construct", International Journal of Molecular Medicine, vol. 8, No. 1, pp. 19-30 (Jul. 2001) (Abstract).

Gordon, E.M., and Hall, F.L., "Rexin-G, a targeted genetic medicine for cancer", Expert Opinion on Biological Therapy, vol. 10, No. 5, pp. 819-832 (2010) (Abstract).

Gordon, E.M., et al., "Inhibition of Metastatic Tumor Growth in Nude Mice by Portal Vein Infusions of Matrix-Targeted Retroviral Vectors Bearing a Cytocidal Cyclin G1 Construct", Cancer Research, vol. 60, No. 13, pp. 3343-3347 (Jul. 1, 2000).

Gordon, E.M., et al., "Systemic Administration of a Matrix-Targeted Retroviral Vector Is Efficacious for Cancer Gene Therapy in Mice", Human Gene Therapy, vol. 12, No. 2, pp. 193-204 (2001).

Gordon, E.M., et al., "First clinical experience using a 'pathotropic' injectable retroviral vector (Rexin-G) as intervention for stage IV pancreatic cancer", International Journal of Oncology, vol. 24, No. 1, pp. 177-185 (Feb. 2004) (Abstract).

Gordon, E.M., et al., "Pathotropic nanoparticles for cancer gene therapy Rexin-G IV: three-year clinical experience", International Journal of Oncology, vol. 29, No. 5, pp. 1053-1064 (Nov. 2006).

Galanis, E., et al., "Phase I Trial of a Pathotropic Retroviral Vector Expressing a Cytocidal Cyclin G1 Construct (Rexin-G) in Patients with Advanced Pancreatic Cancer", Molecular Therapy, vol. 16, No. 5, pp. 979-984 (May 2008).

Chawla, S.P, et al., "Phase I/II and Phase II Studies of Targeted Gene Delivery In Vivo: Intravenous Rexin-G for Chemotherapy-Resistant Sarcoma and Osteosarcoma", Molecular Therapy, vol. 17, No. 9, pp. 1651-1657 (Sep. 2009).

Chawla, S.P, et al., "Advanced Phase I/II Studies of Targeted Gene Delivery In Vivo: Intravenous Rexin-G for Gemcitabine-resistant Metastatic Pancreatic Cancer", Molecular Therapy, vol. 18, No. 2, pp. 435-441 (Feb. 2010).

Kim, S., "Rexin-GR, a tumor-targeted retrovector for malignant peripheral nerve sheath tumor: A case report", Molecular and Clinical Oncology, vol. 6, No. 6, pp. 861-865 (2017).

Burris 3rd, H.A., et al., "Improvements in survival and clinical benefit with gemcitabine as first-line therapy for patients with advanced pancreas cancer: a randomized trial", Journal of Clinical Oncology, vol. 15, No. 6, pp. 2403-2413 (Jun. 1, 1997) (Abstract).

Berlin, J.D., et al., "Phase III study of Gemcitabine in Combination With Fluorouracil Versus Gemcitabine Alone in Patients With Advanced Pancreatic Carcinoma: Eastern Cooperative Oncology Group Trial E2297", Journal of Clinical Oncology, vol. 20, No. 15, pp. 3270-3275 (Aug. 1, 2002) (Abstract).

Lima, C.M.R., et al., "Irinotecan Plus Gemicitabine Results in No Survival Advantage Compared With Gemcitabine Monotherapy in Patients With Locally Advanced or Metastatic Pancreatic Cancer Despite Increased Tumor Response Rate", Journal of Clinical Oncology, vol. 22, No. 18, pp. 3776-3783 (Sep. 15, 2004).

Heinemann, V., et al., "Randomized phase III Trial of Gemcitabine Plus Cisplatin Compared With Gemcitabine Alone in Advanced Pancreatic Cancer", Journal of Clinical Oncology, vol. 24, No. 24, pp. 3946-3952 (Aug. 20, 2006).

Colucci, G., et al., "Gemcitabine Alone or with Cisplatin for the Treatment of Patients with Locally Advanced and/or Metastatic Pancreatic Carcinoma: a Prospective, Randomized Phase III Study of the Gruppo Oncologia dell'Italia Meridionale", Cancer, vol. 94, No. 4, pp. 902-910 (Feb. 15, 2002).

Louvet, C., et al., "Gemcitabine in Combination With Oxaliplatin Compared With Gemcitabine Alone in Locally Advanced or Metastatic Pancreatic Cancer: Results of a GERCOR and GISCAD phase III trial", Journal of Clinical Oncology, vol. 23, No. 15, pp. 3509-3516 (May 20, 2005).

Poplin, E., et al., "Phase III, Randomized Study of Gemcitabine and Oxaliplatin Versus Gemcitabine (fixed-dose rate infusion) Compared with Gemcitabine (30-minute infusion) in Patients with Pancreatic Carcinoma E6201: a Trial of the Eastern Cooperative Oncology Group", Journal of Clinical Oncology, vol. 27, No. 23, pp. 3778-3785 (Aug. 10, 2009).

Herrmann, R., et al., "Gemcitabine Plus Capecitabine Compared with Gemcitabine Alone in Advanced Pancreatic Cancer: A Randomized, Multicenter, Phase III Trial of the Swiss Group for Clinical Cancer Research and the Central European Cooperative Oncology Group", Journal of Clinical Oncology, vol. 25, No. 16, pp. 2212-2217 (Jun. 1, 2007).

Burris 3rd, H., and Rocha-Lima, C., "New Therapeutic Directions for Advanced Pancreatic Cancer: Targeting the Epidermal Growth Factor and Vascular Endothelial Growth Factor Pathways", The Oncologist, vol. 13, No. 3, pp. 289-298 (Mar. 2008).

Senderowicz, A.M., et al., "Erlotinib/gemcitabine for first-line treatment of locally advanced or metastatic adenocarcinoma of the pancreas", Oncology (Williston Park), vol. 21, No. 14, 1696-706 (2007) (Abstract).

Schuetz, T., et al., "Extended survival in second-line pancreatic cancer after therapeutic vaccination", Journal of Clinical Oncology, vol. 23, No. 16, (Jun. 2005) (Abstract).

Petrulio, C.A., and Kaufman, H.L., "Development of the PANVAC-VF vaccine for pancreatic cancer", Expert Review of Vaccines, vol. 5, No. 1, pp. 9-19 (2006) (Abstract).

Gordon, E.M., et al., "Cell cycle checkpoint control: The cyclin G1/Mdm2/p53 axis emerges as a strategic target for broad-spectrum

(56) References Cited

OTHER PUBLICATIONS cancer gene therapy—A review of molecular mechanisms for oncologists", Molecular and Clinical Oncology, vol. 9, No. 2, pp. 115-134 (2018).

Ravicz, J., et al., "Differential expression of human cyclin G1 (CCNG1) in cancer: A novel biomarker in development for CCNG1 inhibitor therapy", Journal of Clinical Oncology, vol. 36, No. 15 (2018) (Abstract).

Hall, F.L., et al., "Pathotropic targeting advances clinical oncology: Tumor-targeted localization of therapeutic gene delivery", Oncology Reports, vol. 24, No. 4, pp. 829-833 (2010).

"Supplemental Guidance on Testing for Replication Competent Retrovirus in Retroviral Vector Based Gene Therapy Products and During Follow-up of Patients in Clinical Trials Using Retroviral Vectors", FDA guidance for industry, Food and Drug Administration, pp. 1-15 (Nov. 2006).

"Common Terminology Criteria for Adverse Events v3.0 (CTCAE)", Cancer Therapy Evaluation Program, Common Terminology Criteria for Adverse Events, Version 3.0, DCTD, NCI, NIH, DHHS, pp. 1-72 (Mar. 31, 2003) published (Aug. 9, 2006).

Therasse, P., et al., "New Guidelines to Evaluate the Response to Treatment in Solid Tumors" European Organization for Research and Treatment of Cancer, National Cancer Institute of the United States, National Cancer Institute of Canada, Journal of the National Cancer Institute, vol. 92, No. 3, pp. 205-216 (Feb. 2, 2000).

Young, H., et al., "Measurement of clinical and subclinical tumour response using [18F]-fluorodeoxyglucose and positron emission tomography: review and 1999 EORTC recommendations. European Organization for Research and Treatment of Cancer (EORTC) PET Study Group", European Journal of Cancer, vol. 35, No. 13, pp. 1773-1782 (Dec. 1999) (Abstract).

Choi, H., et al., "Correlation of Computed Tomography and Positron Emission Tomography in Patients With Metastatic Gastrointestinal Stromal Tumor Treated at a Single Institution With Imatinib Mesylate: Proposal of New Computed Tomography Response Criteria", Journal of Clinical Oncology, vol. 25, No. 13, pp. 1753-1759 (May 1, 2007).

Dy, P.S.G., et al., "Immune cell trafficking in the tumor microenvironment of human cyclin G1 (CCNG1) inhibitor-treated tumors", British Journal of Cancer Research, vol. 1, No. 4, pp. 202-207 (2018).

Gordon, E.M., and Hall, F.L., U.S. Appl. No. 62/454,775, "Targeting the Signature (SIG) of Invading Tumors Using Sig Binding Peptides" (Feb. 4, 2017).

Chen, D.S., et al., "Retroviral Vector-Mediated Transfer of an Antisense Cyclin G1 Construct Inhibits Osteosarcoma Tumor Growth in Nude Mice", Human Gene Therapy, vol. 8, No. 14, pp. 1667-1674 (Sep. 20, 1997).

Cech, T.R., "The RNA Worlds in Context", Cold Spring Harbor Laboratory Press, vol. 4, No. 7, pp. 1-5 (2012).

Hall, F., et al., "Neoplastic transformation in the planarian: I. Cocarcinogenesis and histopathology", Journal of Experimental Zoology, vol. 240, No. 2, pp. 211-227 (Nov. 1986) (Abstract).

Hall, F., et al., "Neoplastic transformation in the planarian: II. Ultrastructure of malignant reticuloma", Journal of Experimental Zoology, vol. 240, No. 2, pp. 229-244 (Nov. 1986) (Abstract).

Morita, .M., "Structure and function of the reticular cell in the planarian Dugesia dorotocephala", Biology of Turbellaria and some Related Flatworms, pp. 189-196 (1995) (Abstract).

Oviedo, N.J., and Beane, W.S., "Regeneration: The Origin of Cancer or a Possible Cure?", Seminars in Cell and Developmental Biology, vol. 20, No. 5, pp. 557-564 (Jul. 2009).

Vulliet, P.R., et al., "Identification of a Novel Proline-Directed Serine/Threonine Protein Kinase in Rat Pheochromocytoma", The Journal of Biological Chemistry, vol. 264, No. 27, pp. 16292-16298 (Sep. 25, 1989).

Hall, F.L., et al., "Phosphorylation of synapsin I at a novel site by proline-directed protein kinase", The Journal of Biological Chemistry, vol. 265, No. 12, pp. 6944-6948 (Apr. 25, 1990).

Hall, F.L., and Vulliet, P.R., "Proline-directed protein phosphorylation and cell cycle regulation", Current Opinion in Cell Biology, vol. 3, No. 2, pp. 176-184 (Apr. 1991) (Abstract).

Lu, K.P., et al., "Pinning down proline-directed phosphorylation signaling", Trends in Cell Biology, vol. 12, No. 4, pp. 164-172 (Apr. 1, 2002).

Lu, Z., and Hunter, T., "Prolyl isomerase Pin1 in cancer", Cell Research, vol. 24, No. 9, pp. 1033-1049 (Sep. 2014).

Hall, F., et al., "Phenotypic differentiation of TGF-beta1-responsive pluripotent premesenchymal prehematopoietic progenitor (P4 stem) cells from murine bone marrow", Journal of Hematotherapy & Stem Cell Research, vol. 10, No. 2, (Jul. 9, 2004) (Abstract).

Yee, A., et al., "Molecular cloning of CDK7-associated human MAT1, a cyclin-dependent kinase-activating kinase (CAK) assembly factor", Cancer Research, vol. 55, No. 24, pp. 6058-6062 (Dec. 15, 1995).

Xu, F., et al., "Molecular cloning and characterization of FX3, a novel zinc-finger protein", Oncology Reports, vol. 7, No. 5, pp. 995-1001 (Sep.-Oct. 2000) (Abstract).

Gordon, E.M., et al., "Targeting metastatic cancer from the inside: a new generation of targeted gene delivery vectors enables personalized cancer vaccination in situ", International Journal of Oncology, vol. 33, No. 4, pp. 665-675 (2008).

Hall, F.L., "Targeting Monoclonal Antibodies to the Tumor Microenvironment for Cancer Therapy/Immunotherapy", Journal of Immunology and Serum Biology, vol. 2, No. 1, pp. 1-7 (2016).

Ignacio G, J., et al., "The Genevieve Protocol: Phase I/II Evaluation of a Dual Targeted Approach to Cancer Gene Therapy/Immunotherapy", Clinics in Oncology, vol. 3, Article 1537, pp. 1-7 (2018).

Yasutis, K.M., and Kozminski, K.G., "Cell cycle checkpoint regulators reach a zillion", Cell Cycle, vol. 12, No. 10, pp. 1501-1509 (May 15, 2013).

Horne, M.C., et al., Cyclin G1 and cyclin G2 comprise a new family of cyclins with contrasting tissue-specific and cell cycle-regulated expression, The Journal of Biological Chemistry, vol. 271, No. 11, pp. 6050-6061 (Mar. 15, 1996).

Chen, X., "Cyclin G: a regulator of the p53-Mdm2 network", Developmental Cell, vol. 2, No. 5, pp. 518-519 (May 2002).

Sinha, A.U., et al., "Dissecting microregulation of a master regulatory network", BMC Genomics, vol. 9, No. 88, pp. 1-19 (2008).

Ohtsuka, T., et al., "Modulation of p53 and p73 levels by cyclin G: implication of a negative feedback regulation", Oncogene, vol. 22, pp. 1678-1687 (2003).

Hager, K.M., and Wei, G., "Understanding the non-canonical pathways involved in p53-mediated tumor suppression", Carcinogenesis, vol. 35, No. 4, pp. 740-746 (Apr. 2014).

Hydbring, P., et al., "Non-canonical functions of cell cycle cyclins and cyclin-dependent kinases", Nature Reviews Molecular Cell Biology, vol. 17, No. 5, pp. 280-292 (May 2016).

Bayer, F.E., et al., "p53 and cyclin G cooperate in mediating genome stability in somatic cells of *Drosophila*", Scientific Reports, vol. 7, Article No. 17890, pp. 1-15 (2017).

Chawla, S.P., et al., "A Phase I-II Study Using Rexin-G Tumor-Targeted Retrovector Encoding a Dominant-Negative Cyclin G1 Inhibitor for Advanced Pancreatic Cancer", Molecular Therapy: Oncolytics, vol. 12, pp. 56-67 (Mar. 29, 2019).

Chawla, S.P., et al., "An Advanced Phase 1/2 Study using an XC-Targeted Gene Therapy Vector for Chemotherapy Resistant Sarcoma", Sarcoma Research—International, vol. 3, No. 1, pp. 1-7 (2016).

Gordon, E.M., et al., "Le morte du tumour: histological features of tumor destruction in chemo-resistant cancers following intravenous infusions of pathotropic nanoparticles bearing therapeutic genes", International Journal of Oncology, vol. 30, No. 6, pp. 1297-1307 (2007).

Gordon, E.M., and Hall, F.L., "Critical Stages in the Development of the First Targeted, Injectable Molecular-Genetic Medicine for Cancer", Gene Therapy Application, pp. 461-492 (Aug. 23, 2011).

Xu, Y., et al., "CCNG1 (Cyclin G1) regulation by mutant-P53 via induction of Notch3 expression promotes high-grade serous ovarian cancer (HGSOC) tumorigenesis and progression" Cancer Medicine, vol. 8, No. 1, pp. 351-362 (2019).

(56) References Cited

OTHER PUBLICATIONS

Luan, Y., et al., "Cyclin G1 mediates the poor prognosis of breast cancer through expanding the cancer stem cells", International Journal of Clinical and Experimental Medicine, vol. 12, No. 5, pp. 5475-5486 (2019).
Wang, M., "Kidney Fibrosis-Cyclin G1 drives maladaptive renal repair", Nature Reviews | Nephrology, vol. 15, p. 191 (Apr. 2019).
Canaud, G., et al., "Cyclin G1 and TASCC regulate kidney epithelial cell G2-M arrest and fibrotic maladaptive repair", Science Translational Medicine, vol. 11, No. 476, pp. 1-33 (Jan. 23, 2019).
Sheridan, P.L., et al., "Generation of Retroviral Packaging and Producer Cell Lines for Large-Scale Vector Production and Clinical Application: Improved Safety and High Titer", Molecular Therapy, vol. 2, No. 3, pp. 262-275 (Sep. 2000).
Van Der Loo, J.C.M., and Wright, J.F., "Progress and challenges in viral vector manufacturing", Human Molecular Genetics, vol. 25, No. R1, pp. 1-11 (Oct. 30, 2015).
Merten, O.W., et al., "Production of lentiviral vectors", Molecular Therapy—Methods & Clinical Development, vol. 3, No. 16017, pp. 1-14 (2016).
Jordan, M., et al., "Transfecting mammalian cells: optimization of critical parameters affecting calcium-phosphate precipitate formation", Nucleic Acids Research, vol. 24, No. 4, pp. 596-601 (1996).
Kearney, B.J., et al., "Corning HYPERFlask® for viral amplification and production of diagnostic reagents", Journal of Virological Methods, vol. 242, pp. 9-13, (Apr. 2017) (Abstract).
"Epeius Biotechnologies Corporation Expands its Rexin-G Production Facilities in Southern California", Epeius Biotechnologies, p. 1 (Feb. 19, 2010).
Rutteman, G.R., et al., "Safety and efficacy field study of artesunate for dogs with non-resectable tumours", Anticancer Research, vol. 33, No. 5, pp. 1819-1827 (2013).
Breuer, E., and Efferth, T., "Treatment of Iron-Loaded Veterinary Sarcoma by Artemisia annua", Natural Products and Bioprospecting, vol. 4, pp. 113-118 (2014).
Efferth, T., "Cancer combination therapies with artemisinin-type drugs", Biochemical Pharmacology, vol. 139, pp. 56-70 (2017).
Bruckner, H.W., "Phase I-II study using DeltaRex-G, a tumor-targeted retrovector encoding a cyclin G1 inhibitor for metastatic carcinoma of breast", Frontiers in Molecular Medicine, vol. 3, pp. 1-10 (May 18, 2023).
Chawla, S.P., et al., "Early-stage CCNG1+ Hr+ HER2+ Invasive Breast Carcinoma in Older Women: Current Treatment and Future Perspectives for DeltaRex-G, a CCNG1 Inhibitor", Anticancer Research, vol. 43, No. 6, pp. 2383-2391 (2023).
Liu, S., et al., "Long Term Survival Following DeltaRex-G/DeltaVax Tumor-Targeted Gene Therapy for Advanced Chemotherapy-Resistant Malignancies: An Academic Milestone", Clinics in Oncology, vol. 6, Article 1807, pp. 1-7 (2021).
Morse, M.A., et al., "Tumor protein p53 mutation in archived tumor samples from a 12-year survivor of stage 4 pancreatic ductal adenocarcinoma may predict long-term survival with DeltaRex-G: A case report and literature review", Molecular and Clinical Oncology, vol. 15, No. 3, pp. 1-7 (2021).
Cuadrado, A., et al., "A new p38 MAP kinase-regulated transcriptional coactivator that stimulates p53-dependent apoptosis", European Molecular Biology Organization, vol. 26, No. 8, pp. 2115-2126 (2007).
Lafarga, V., et al., "p18(Hamlet) mediates different p53-dependent responses to DNA-damage inducing agents", Cell Cycle, vol. 6, No. 19, pp. 2319-2322 (Oct. 1, 2007).
Segalés, J., et al., "Regulation of Muscle Stem Cell Functions: A Focus on the p38 MAPK Signaling Pathway", Frontiers in Cell and Developmental Biology, vol. 4, Article 91, pp. 1-15 (Aug. 2016).
Cuadrado, A., et al., "Essential role of p18Hamlet/SRCAP-mediated histone H2A.Z chromatin incorporation in muscle differentiation", European Molecular Biology Organization, vol. 29, No. 12, pp. 2014-2025 (2010).

Gramantieri, L., et al., "Cyclin G1 Is a Target of miR-122a, a MicroRNA Frequently Down-regulated in Human Hepatocellular Carcinoma", Cancer Research, vol. 67, No. 13, pp. 6092-6099 (2007).
Yan, J., et al., "MiR-23b targets cyclin G1 and suppresses ovarian cancer tumorigenesis and progression", Journal of Experimental & Clinical Cancer Research, vol. 35, Article No. 31, pp. 1-10 (2016).
Han, H., et al., "MiR-23b suppresses lung carcinoma cell proliferation through CCNG1", Oncology Letters, vol. 16, pp. 4317-4324 (2018).
Shang, Y., et al., "The miR27b-CCNG1-P53-miR-508-5p axis regulates multidrug resistance of gastric cancer", Oncotarget, vol. 7, No. 1, pp. 538-549 (2015).
Seo, H.R., et al., "Cdk5-mediated Phosphorylation of c-Myc on Ser-62 Is Essential in Transcriptional Activation of Cyclin B1 by Cyclin G1", The Journal of Biological Chemistry, vol. 283, No. 23, pp. 15601-15610 (Jun. 6, 2008).
Hydbring, P., et al., "MYC Modulation around the CDK2/p27/SKP2 Axis", Genes, vol. 8, No. 7, pp. 1-32 (Jun. 30, 2017).
Balasubramanian, A., et al., "BRD7 Promoter Hypermethylation as an Indicator of Well Differentiated Oral Squamous Cell Carcinomas", Asian Pacific Journal of Cancer Prevention, vol. 16, No. 4, pp. 1615-1619 (2015).
Yu, X., and Li, Z., "Long non-coding Rna Hotair: A novel oncogene (Review)", Molecular Medicine Reports, vol. 12, No. 4, pp. 5611-5618 (2015).
Cheng, D., et al., "LncRNA HOTAIR epigenetically suppresses miR-122 expression in hepatocellular carcinoma via DNA methylation", EBioMedicine, vol. 36, pp. 159-170 (2018).
Bandopadhyay, M., et al., "Hepatitis B virus X protein mediated suppression of miRNA-122 expression enhances hepatoblastoma cell proliferation through cyclin G1-p53 axis", Infectious Agents and Cancer, vol. 11, Article No. 40, pp. 1-12 (2016).
Gordon, E.M., and Hall, F.L., "Nanotechnology blooms, at last (Review)", Oncology Reports, vol. 13, No. 6, pp. 1003-1007 (2005).
Gordon, E.M., and Hall, F.L., "The 'timely' development of Rexin-G: First targeted injectable gene vector (Review)", International Journal of Oncology, vol. 35, No. 2, pp. 229-238 (2009).
Gordon, E.M., and Hall, F.L., "Noteworthy clinical case studies in cancer gene therapy: Tumor-targeted Rexin-G advances as an efficacious anti-cancer agent", International Journal of Oncology, vol. 36, No. 6, pp. 1341-1353 (2010).
Langreth, R., et al., "Researchers Get Dose of Reality As Logistics Stymie Gene Therapy", The Wall Street Journal, p. 1, (Oct. 27, 1999).
Wyrwicz, L.S., et al., "A common cis-element in promoters of protein synthesis and cell cycle genes", Acta Biochimica Polonica, vol. 54, No. 1, pp. 89-98 (2007).
Žiberna, L., et al., "Oleanolic Acid Alters Multiple Cell Signaling Pathways: Implication in Cancer Prevention and Therapy", International Journal of Molecular Sciences, vol. 18, No. 3, Article No. 643, pp. 1-16 (2017).
Peron, G., et al., "Known Triterpenes and their Derivatives as Scaffolds for the Development of New Therapeutic Agents for Cancer", Current Medicinal Chemistry, vol. 25, No. 10, pp. 1259-1269 (2018).
Zhao, X., et al., "Oleanolic acid suppresses the proliferation of lung carcinoma cells by miR-122/Cyclin G1/MEF2D axis", Molecular and Cellular Biochemistry, vol. 400, No. 1-2, pp. 1-7, (2015).
International Search Report and Written Opinion as issued in connection with International Patent Application No. PCT/US2019/066968, mailed Mar. 2, 2020, 7 pages.
Gordon, L.M., et al., "First clinical experience using a 'pathotropic' injectable retroviral vector (Rexin-G) as intervention for stage IV pancreatic cancer", International Journal of Oncology, vol. 24, pp. 177-185, (2004).

* cited by examiner

ALPHA-5-HELIX DOMAIN (Boxed Area)

```
Cyclin A:   285- TYTKKQVLRMEHLVLKVLTFDL -306  (SEQ ID NO:4)
Cyclin B1:       TYTKHQIRQMEMKILRAINFGL         (SEQ ID NO:5)
Cyclin D1:       SIRPEELLQMELLLVNKLKWNL         (SEQ ID NO:6)
Cyclin D2:       SIKPQELLEWELVVLGKLKWNLAA       (SEQ ID NO:7)
Cyclin-E1:       ACSGDEILTMELMIMKALKWRL         (SEQ ID NO:8)
Cyclin G1:  128- RETVSDLMRMEKIVLEKVCWKVKAT      (SEQ ID NO:9)  Δ problematic Cys/T P35-Cip$^{p5}$: 254- KEAFWDRCLSVINLMSSKMLQINA    (SEQ ID NO:10) Δ problematic Cys/T
```

CDK5 inhibitor$^{p5}$ in post-mitotic nervous system bears little homology

FIG. 4A

CYCLIN G1/DNG1 MDM2-BINDING DOMAIN (CPP shown in bold)

```
Cyclin G1:   187- KACHCRIIFSKAKPSVLALSIIALEIQAQKCV -217   (SEQ ID NO:11)

Test peptides
Cyclin G1$^{inf.}$: 187- KACHCRIIFSKAKPSVLALSIIAYGRKKRRQRRR   (SEQ ID NO:12)  34 aa
Cyclin G1$^{(-)}$:  192- RIIFSKAKPSVLALSIIALEIQAYGRKKRRQRRR   (SEQ ID NO:13)  34 aa
```

FIG. 4B

CYCLIN G1/DNG1 PP2A-BINDING DOMAIN (CPP shown in bold)

ELAS1 Peptide: RQLKHSYYRITHLPTIPEMVPYGRKKRRQRRR (SEQ ID NO:14) 32 aa

*FIG. 4C*

α5-Helix
Cyclin A:    285 – TYTKKQVLRMEHLVLKVLTFDYGRKKRRQRRR (SEQ ID NO:15) 32 aa
Cyclin D1:         SIRPEELLLQMELLLVNKLKWNYGRKKRRQRRR (SEQ ID NO:16) 32 aa
Cyclin D2^FLH:     SIKPQELLEWELVVLGKLKWNYGRKKRRQRRR (SEQ ID NO:17) 32 aa
Cyclin E:          AMSGDEILTMELMIMKALKWRYGRKKRRQRRR (SEQ ID NO:18) 32 aa
Cyclin G1:    128 – RFTVSDLMRMEKIVLEKVTWKYGRKKRRQRRR (SEQ ID NO:19) 32 aa

Mdm2-Domain
Cyclin G1*:  187 – KACHCRTIFSKAKPSVLALSIIAYGRKKRRQRRR (SEQ ID NO:12) 34 aa
Cyclin G1*:  192 – RTIFSKAKPSVLALSIIALETQAYGRKKRRQRRR (SEQ ID NO:13) 34 aa

PP2A-Domain
Cyclin G1:   275 – RQLKHSYYRITHLPTIPEMVPYGRKKRRQRRR (SEQ ID NO:14) 32 aa Myc-Tag_control:   SVQAEEQKLISEEDLLRKRRE YGRKKRRQRRR (SEQ ID NO:20) 32 aa

*FIG. 4D*

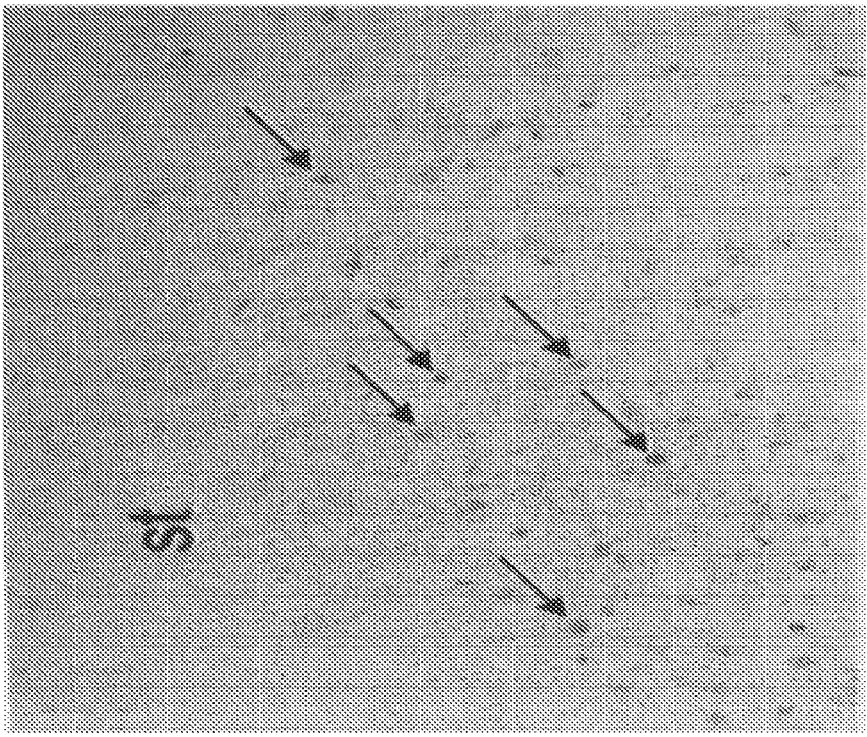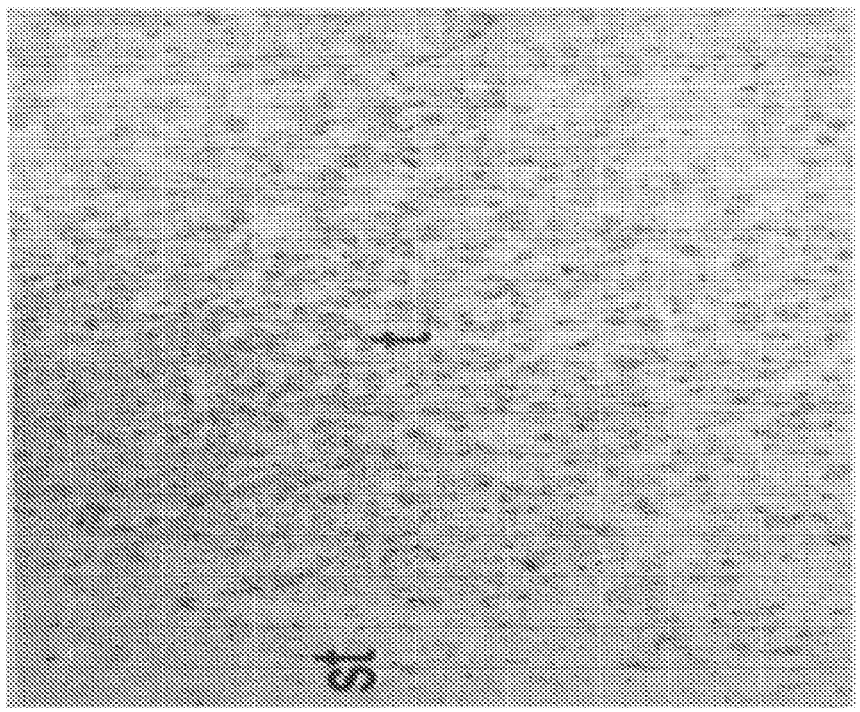
FIG. 5

SEQUENCE LISTING

```
<160> NUMBER OF SEQ ID NOS: 25

<210> SEQ ID NO 1
<211> LENGTH: 10
<212> TYPE: PRT
<213> ORGANISM: Homo sapiens

<400> SEQUENCE: 1

Trp Arg Glu Pro Ser Phe Met Ala Leu Ser
1               5                   10

<210> SEQ ID NO 2
<211> LENGTH: 10
<212> TYPE: PRT
<213> ORGANISM: Homo sapiens

<400> SEQUENCE: 2

Trp Arg Glu Pro Gly Arg Met Glu Leu Asn
1               5                   10

<210> SEQ ID NO 3
<211> LENGTH: 9
<212> TYPE: PRT
```

```
<213> ORGANISM: Artificial Sequence
<220> FEATURE:
<223> OTHER INFORMATION: Collagen repeat
<220> FEATURE:
<221> NAME/KEY: MISC_FEATURE
<222> LOCATION: (2)..(2)
<223> OTHER INFORMATION: Xaa is an amino acid other than Gly, Pro, or
      Hyp
<220> FEATURE:
<221> NAME/KEY: MISC_FEATURE
<222> LOCATION: (3)..(3)
<223> OTHER INFORMATION: Xaa is Pro or Hyp
<220> FEATURE:
<221> NAME/KEY: MISC_FEATURE
<222> LOCATION: (5)..(5)
<223> OTHER INFORMATION: Xaa is an amino acid other than Gly, Pro, or
      Hyp
<220> FEATURE:
<221> NAME/KEY: MISC_FEATURE
<222> LOCATION: (6)..(6)
<223> OTHER INFORMATION: Xaa is Pro or Hyp
<220> FEATURE:
<221> NAME/KEY: MISC_FEATURE
<222> LOCATION: (8)..(8)
<223> OTHER INFORMATION: Xaa is an amino acid other than Gly, Pro, or
      Hyp
<220> FEATURE:
<221> NAME/KEY: MISC_FEATURE
<222> LOCATION: (9)..(9)
<223> OTHER INFORMATION: Xaa is Pro or Hyp

<400> SEQUENCE: 3

Gly Xaa Xaa Ala Xaa Xaa Gly Xaa Xaa
1               5

<210> SEQ ID NO 4
<211> LENGTH: 22
<212> TYPE: PRT
<213> ORGANISM: Homo sapiens

<400> SEQUENCE: 4

Thr Tyr Thr Lys Lys Gln Val Leu Arg Met Glu His Leu Val Leu Lys
1               5                   10                  15

Val Leu Thr Phe Asp Leu
            20

<210> SEQ ID NO 5
<211> LENGTH: 22
<212> TYPE: PRT
<213> ORGANISM: Homo sapiens

<400> SEQUENCE: 5

Thr Tyr Thr Lys His Gln Ile Arg Gln Met Glu Met Lys Ile Leu Arg
1               5                   10                  15

Ala Leu Asn Phe Gly Leu
            20

<210> SEQ ID NO 6
<211> LENGTH: 22
<212> TYPE: PRT
<213> ORGANISM: Homo sapiens

<400> SEQUENCE: 6

Ser Ile Arg Pro Glu Glu Leu Leu Gln Met Glu Leu Leu Leu Val Asn
1               5                   10                  15

Lys Leu Lys Trp Asn Leu
            20
```

```
<210> SEQ ID NO 7
<211> LENGTH: 24
<212> TYPE: PRT
<213> ORGANISM: Homo sapiens

<400> SEQUENCE: 7

Ser Ile Lys Pro Gln Glu Leu Leu Glu Trp Glu Leu Val Val Leu Gly
1               5                   10                  15

Lys Leu Lys Trp Asn Leu Ala Ala
            20

<210> SEQ ID NO 8
<211> LENGTH: 22
<212> TYPE: PRT
<213> ORGANISM: Homo sapiens

<400> SEQUENCE: 8

Ala Cys Ser Gly Asp Glu Ile Leu Thr Met Glu Leu Met Ile Met Lys
1               5                   10                  15

Ala Leu Lys Trp Arg Leu
            20

<210> SEQ ID NO 9
<211> LENGTH: 25
<212> TYPE: PRT
<213> ORGANISM: Homo sapiens

<400> SEQUENCE: 9

Arg Phe Thr Val Ser Asp Leu Met Arg Met Glu Lys Ile Val Leu Glu
1               5                   10                  15

Lys Val Cys Trp Lys Val Lys Ala Thr
            20                  25

<210> SEQ ID NO 10
<211> LENGTH: 24
<212> TYPE: PRT
<213> ORGANISM: Homo sapiens

<400> SEQUENCE: 10

Lys Glu Ala Phe Trp Asp Arg Cys Leu Ser Val Ile Asn Leu Met Ser
1               5                   10                  15

Ser Lys Met Leu Gln Ile Asn Ala
            20

<210> SEQ ID NO 11
<211> LENGTH: 32
<212> TYPE: PRT
<213> ORGANISM: Homo sapiens

<400> SEQUENCE: 11

Lys Ala Cys His Cys Arg Ile Ile Phe Ser Lys Ala Lys Pro Ser Val
1               5                   10                  15

Leu Ala Leu Ser Ile Ile Ala Leu Glu Ile Gln Ala Gln Lys Cys Val
            20                  25                  30

<210> SEQ ID NO 12
<211> LENGTH: 34
<212> TYPE: PRT
<213> ORGANISM: Artificial Sequence
<220> FEATURE:
<223> OTHER INFORMATION: Synthetic oligonucleotide

<400> SEQUENCE: 12
```

Lys Ala Cys His Cys Arg Ile Ile Phe Ser Lys Ala Lys Pro Ser Val
1               5                   10                  15

Leu Ala Leu Ser Ile Ile Ala Tyr Gly Arg Lys Lys Arg Gln Arg
            20                  25                  30

Arg Arg

<210> SEQ ID NO 13
<211> LENGTH: 34
<212> TYPE: PRT
<213> ORGANISM: Artificial Sequence
<220> FEATURE:
<223> OTHER INFORMATION: Synthetic oligonucleotide

<400> SEQUENCE: 13

Arg Ile Ile Phe Ser Lys Ala Lys Pro Ser Val Leu Ala Leu Ser Ile
1               5                   10                  15

Ile Ala Leu Glu Ile Gln Ala Tyr Gly Arg Lys Lys Arg Gln Arg
            20                  25                  30

Arg Arg

<210> SEQ ID NO 14
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 14

Arg Gln Leu Lys His Ser Tyr Tyr Arg Ile Thr His Leu Pro Thr Ile
1               5                   10                  15

Pro Glu Met Val Pro Tyr Gly Arg Lys Lys Arg Arg Gln Arg Arg
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 15

Thr Tyr Thr Lys Lys Gln Val Leu Arg Met Glu His Leu Val Leu Lys
1               5                   10                  15

Val Leu Thr Phe Asp Tyr Gly Arg Lys Lys Arg Arg Gln Arg Arg
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 16

Ser Ile Arg Pro Glu Glu Leu Leu Gln Met Glu Leu Leu Leu Val Asn
1               5                   10                  15

Lys Leu Lys Trp Asn Tyr Gly Arg Lys Lys Arg Gln Arg Arg
            20                  25                  30

<210> SEQ ID NO 17
<211> LENGTH: 32
<212> TYPE: PRT
<213> ORGANISM: Artificial Sequence

```
<220> FEATURE:
<223> OTHER INFORMATION: Synthetic oligonucleotide

<400> SEQUENCE: 17

Ser Ile Lys Pro Gln Glu Leu Leu Glu Trp Glu Leu Val Val Leu Gly
1               5                   10                  15

Lys Leu Lys Trp Asn Tyr Gly Arg Lys Lys Arg Gln Arg Arg
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 18

Ala Met Ser Gly Asp Glu Ile Leu Thr Met Glu Leu Met Ile Met Lys
1               5                   10                  15

Ala Leu Lys Trp Arg Tyr Gly Arg Lys Lys Arg Arg Gln Arg Arg
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 19

Arg Phe Thr Val Ser Asp Leu Met Arg Met Glu Lys Ile Val Leu Glu
1               5                   10                  15

Lys Val Thr Trp Lys Tyr Gly Arg Lys Lys Arg Gln Arg Arg
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Synthetic oligonucleotide

<400> SEQUENCE: 20

Ser Val Gln Ala Glu Glu Gln Lys Leu Ile Ser Glu Glu Asp Leu Leu
1               5                   10                  15

Arg Lys Arg Arg Glu Tyr Gly Arg Lys Lys Arg Gln Arg Arg
            20                  25                  30

<210> SEQ ID NO 21
<211> LENGTH: 11
<212> TYPE: PRT
<213> ORGANISM: Artificial Sequence
<220> FEATURE:
<223> OTHER INFORMATION: Synthetic oligonucleotide

<400> SEQUENCE: 21

Tyr Gly Arg Lys Lys Arg Arg Gln Arg Arg Arg
1               5                   10

<210> SEQ ID NO 22
<211> LENGTH: 21
<212> TYPE: PRT
<213> ORGANISM: Artificial Sequence
<220> FEATURE:
<223> OTHER INFORMATION: Synthetic oligonucleotide
```

-continued

```
<400> SEQUENCE: 22

Arg Phe Thr Val Ser Asp Leu Met Arg Met Glu Lys Ile Val Leu Glu
1               5                   10                  15

Lys Val Thr Trp Lys
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic oligonucleotide

<400> SEQUENCE: 23

Lys Ala Cys His Cys Arg Ile Ile Phe Ser Lys Ala Lys Pro Ser Val
1               5                   10                  15

Leu Ala Leu Ser Ile Ile Ala
            20

<210> SEQ ID NO 24
<211> LENGTH: 23
<212> TYPE: PRT
<213> ORGANISM: Artificial Sequence
<220> FEATURE:
<223> OTHER INFORMATION: Synthetic oligonucleotide

<400> SEQUENCE: 24

Arg Ile Ile Phe Ser Lys Ala Lys Pro Ser Val Leu Ala Leu Ser Ile
1               5                   10                  15

Ile Ala Leu Glu Ile Gln Ala
            20

<210> SEQ ID NO 25
<211> LENGTH: 21
<212> TYPE: PRT
<213> ORGANISM: Artificial Sequence
<220> FEATURE:
<223> OTHER INFORMATION: Synthetic oligonucleotide

<400> SEQUENCE: 25

Arg Gln Leu Lys His Ser Tyr Tyr Arg Ile Thr His Leu Pro Thr Ile
1               5                   10                  15

Pro Glu Met Val Pro
            20
```

CYCLIN G1 INHIBITORS AND RELATED METHODS OF TREATING CANCER

CROSS-REFERENCE TO RELATED APPLICATIONS

This application is a continuation of U.S. application Ser. No. 16/483,308, filed on Aug. 2, 2019, which is a U.S. National Stage entry of PCT/US2018/016643, filed Feb. 2, 2018 and entitled "CYCLIN G1 INHIBITORS AND RELATED METHODS OF TREATING CANCER," which claims the benefit of U.S. Provisional Application No. 62/533,595, filed on Jul. 17, 2017, and U.S. Provisional Application No. 62/454,775, filed on Feb. 4, 2017, each of which is hereby incorporated by reference in its entirety.

TECHNICAL FIELD

The present disclosure relates generally to methods of treating a cancer. The present disclosure also relates to viral vectors and cell penetrating peptides configured for inhibiting expression of the Cyclin G1 (CCNG1) gene and companion diagnostics for use with such viral vectors and cell penetrating peptides.

BACKGROUND

Cancer is an enormous global health burden, touching every region and socioeconomic group. In 2012, there were an estimated 14.1 million cases of cancer diagnosed around the world and 9.2 million cancer deaths. According to the annual report of the American Cancer Society, in the U.S. there will be an estimated 1,688,780 new cancer cases diagnosed and 600,920 cancer deaths in 2017. Moreover, the global cancer burden is growing at an alarming pace. It is predicted that in 2030 alone, about 21.6 million new cancer cases and 13 million cancer deaths are expected to occur, simply due to the growth and aging of the world's population.

The inherent toxicities of many approved chemotherapeutic agents are a result of the non-specific nature of drug distribution, which also damages normal tissues and organs. Chemotherapies and biologics are distributed widely to both target and non-target organs. Such anticancer agents generally require high plasma levels, which kill both cancer cells and normal cells and thus can be dangerous. This non-targeted biodistribution often results in untoward systemic toxicities which negatively impact the treatment regimen and outcome.

BRIEF DESCRIPTION OF THE DRAWINGS

The embodiments disclosed herein will become more fully apparent from the following description and appended claims, taken in conjunction with the accompanying drawings.

FIG. 1A depicts an MLV-based chimeric viral vector carrier displaying a SIG binding peptide (arrowheads). FIG. 1B depicts the tumor microenvironment wherein SIG proteins are exposed by the invading tumor. FIG. 1C depicts the genetic payload of a viral vector which encodes a dominant negative Cyclin G1 (CCNG1) mutant construct and the herpes simplex thymidine kinase (HStk) gene.

FIG. 4A shows a peptide designed from the α5 Helix domain of Cyclin A to competitively inhibit the activity of Cyclin A/CDK2 and/or Cyclin A/Cdc2 in relation to several other structurally-related but functionally distinct cyclin proteins.

FIG. 4B depicts the Cyclin G1/dnG1 Mdm2-binding domain and two test peptides derived from this region. Each designer peptide is conjoined with a Tat-derived cell penetrating peptide ("CPP" shown in bold) to facilitate intracellular delivery of the blocking peptide.

FIG. 4C shows an extended/optimized version of the C-terminal Cyclin G1-derived peptide (ELAS1, underlined), which more-efficiently blocks the binding of PP2A to Cyclin G1 and potentially results in cellular sensitization to chemotherapies.

FIG. 4D shows an "experimental set" of cell cycle blocking peptides (CCBP) of similar length, designed for direct comparisons, including novel test peptides derived from CyclinG1/dnG1. As indicated, a standard YGRKKRRQRRR (SEQ ID NO:21) Tat-derived cell penetrating peptide sequence (CPP) is appended to the C-terminus of each test peptide—strategically conjoined without extraneous linkers at the indicated hydrophobic amino acids—to produce the linear CCBP-CPP fusion constructs.

FIG. 5 depicts downregulation of CCNG1 expression by DeltaRex-G in a nude mouse model of pancreas cancer (Gordon, et al., Hum Gene Ther 2001; 12:193-204). Human undifferentiated cancer cells of pancreatic origin (MiaPaca2) were implanted subcutaneously into the flanks of nude mice, followed six days later by tail vein injections of DeltaRex-G vector. Arrest of tumor growth occurred after a seven-day treatment cycle of the DeltaRex-G (formerly Mx-dnG1) vector. Note the intense nuclear immunoreactivity for human CCNG1 protein in the tumor nodule (t) from a control vector-treated animal with minimal staining in the capsule (st) (left panel), compared to the markedly reduced immunoreactivity for the human CCNG1 protein in a tumor nodule from the DeltaRex-G vector-treated animal (right panel).

DETAILED DESCRIPTION

The present disclosure relates generally to methods of treating a cancer in a patient. The method can include obtaining a tumor sample from the patient, detecting whether CCNG1 gene expression is present in the tumor sample, diagnosing the patient with a CCNG1 inhibitor-responsive cancer when the presence of CCNG1 gene expression in the tumor sample is detected, and/or administering an effective amount of a CCNG1 inhibitor to the diagnosed patient. The present disclosure also relates to CCNG1 inhibitors including a viral vector having a binding peptide that is configured to bind one or more SIG elements of an invading tumor and at least one cytocidal gene. Cyclin G1 inhibitors including cell cycle blocking peptides (CCBPs) fused with cell penetrating peptides (CPPs) are also disclosed.

It will be readily understood that the embodiments, as generally described herein, are exemplary. The following more detailed description of various embodiments is not intended to limit the scope of the present disclosure, but is merely representative of various embodiments. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified.

Targeting anticancer agents to abnormal signature proteins (i.e., SIG proteins present in invading tumors) can have multiple clinical implications including, but not limited to: (1) directly targeting SIG proteins can result in drug accumulation within an invading tumor, (2) thus, lower drug doses may be needed to kill the cancer cells and/or the associated blood supply, (3) lower drug doses can lessen systemic toxicity, (4) this combination raises the Therapeutic Index, which can improve overall survival, and (5) SIG tumor-targeting can overcome genetic heterogeneity of tumors by focusing on a common feature of the invading tumor (i.e., the SIG elements in the tumor microenvironment).

Figure 1C:
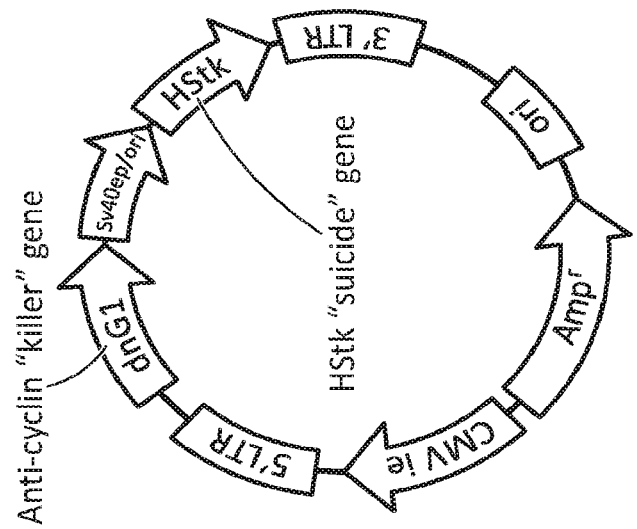
FIGS. 1A-1C depict graphic illustrations of the molecular components of a gene therapy vector that targets the signature (SIG) proteins of invading tumors.
Figure 1B:
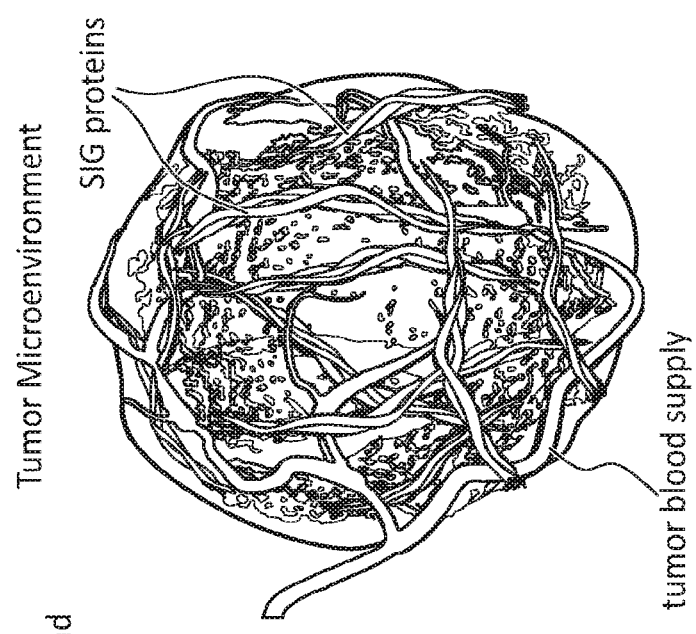
Figure 1A:
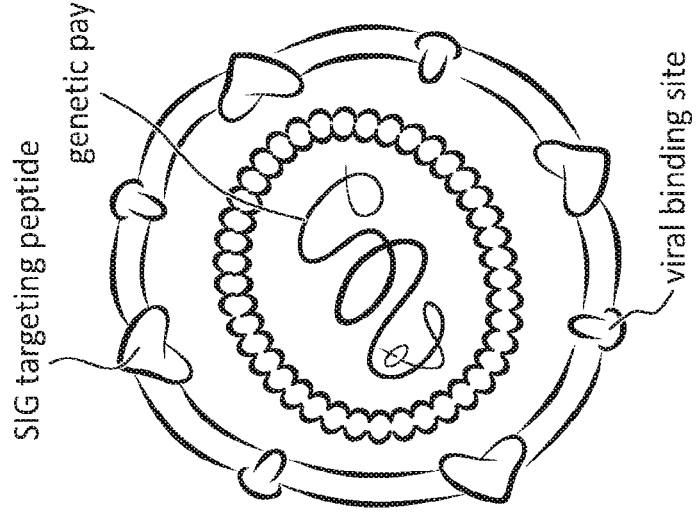

FIGS. 1A-1C depict graphic illustrations of the molecular components of a gene therapy vector that targets the SIGs of invading tumors. FIG. 1A depicts an MLV-based chimeric viral vector carrier displaying a SIG binding peptide (arrowheads). FIG. 1B depicts the tumor microenvironment wherein SIG proteins are exposed by the invading tumor. FIG. 10 depicts the genetic payload which encodes the designer dominant negative CCNG1 mutant construct and the herpes simplex thymidine kinase (HStk) gene. Injected intravenously, the targeted vectors seek out and accumulate in tumors by binding to abnormal SIG proteins in the tumor microenvironment (TME).

Figure 2:
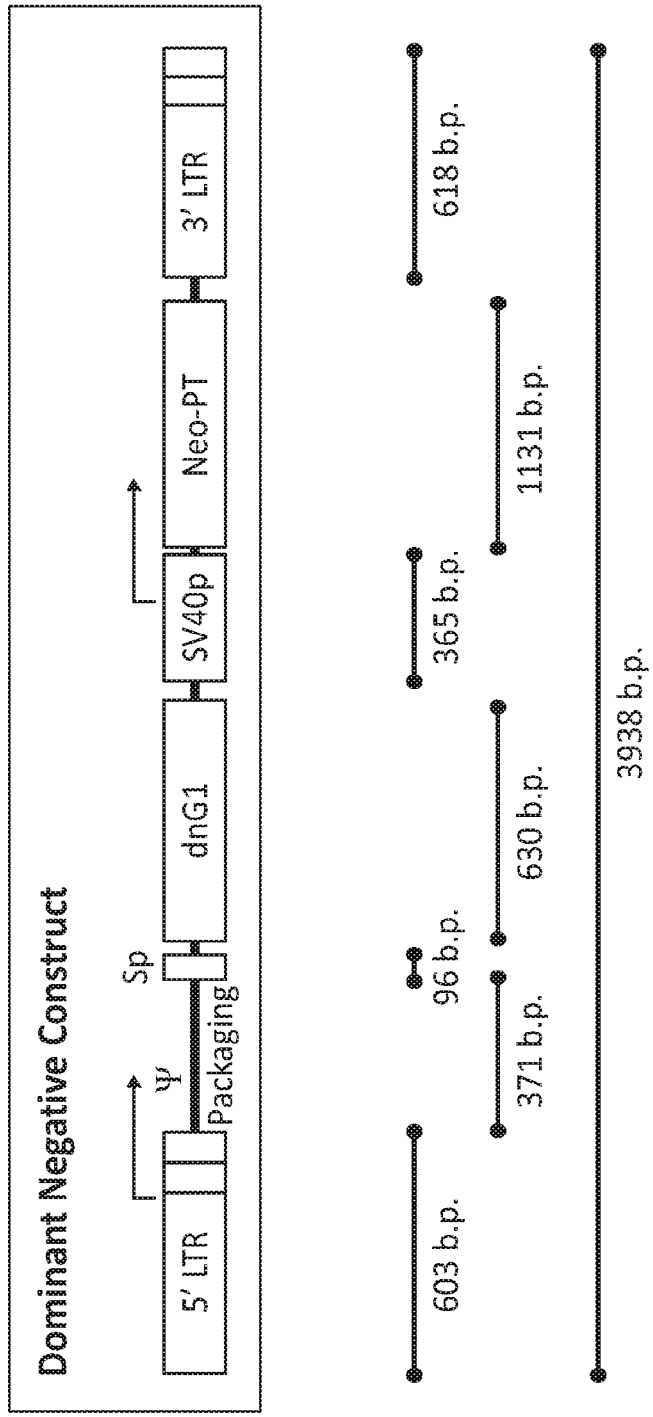
FIG. 2 depicts a graphic illustration of the DeltaRex-G vector. The DeltaRex-G vector, encoding a dominant negative CCNG1 construct, is produced by transient co-transfection with three plasmids of 293T cells obtained from a certified master cell bank. The final product, DeltaRex-G, is a tumor-targeted retrovector that binds to specific SIG sequences in the tumor microenvironment, which augments effective vector concentration in cancerous lesions.

DeltaRex-G (see FIG. 2) is a tumor-targeted, MLV-based nanoparticle (~100 nm) encoding an N-terminal deletion mutant human CCNG1 construct under the control of a hybrid LTR/CMV promoter. The vector also contains the neomycin resistance (neo$^r$) gene which is driven by the SV40 early promoter. The DeltaRex-G vector can be produced by transient co-transfection of three plasmids in 293T (human kidney 293 cells transformed with SV40 large T antigen) producer cells obtained from a fully validated master cell bank.

Figure 3:
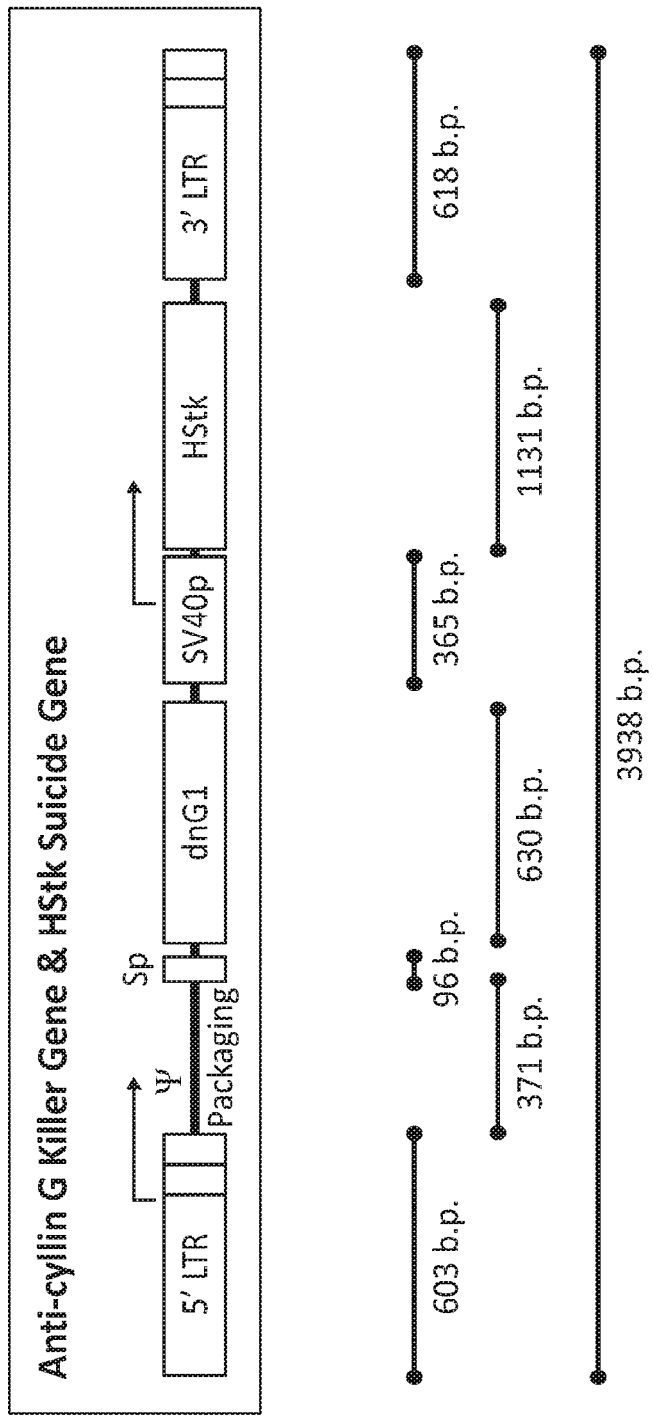
FIG. 3 depicts a graphic illustration of the DeltaRex-GT vector. The DeltaRex-GT vector, encoding a dominant negative CCNG1 construct and an HStk gene, is produced by transient co-transfection with 3 plasmids of 293T cells obtained from a certified master cell bank. The final product, DeltaRex-GT, is a tumor-targeted retrovector that binds to specific SIG sequences in the tumor microenvironment which augments effective vector concentration in cancerous lesions.

DeltaRex-GT (see FIG. 3), a modified version of DeltaRex-G for improved safety and efficacy, is also a tumor-targeted, MLV-based nanoparticle (~100 nm) encoding an N-terminal deletion mutant human CCNG1 construct under the control of a hybrid LTR/CMV promoter. In addition, the vector contains the HStk gene which is driven by the SV40 early promoter. The DeltaRex-GT vector can be produced by transient co-transfection of three plasmids in 293T (human kidney 293 cells transformed with SV40 large T antigen) producer cells obtained from a fully validated master cell bank.

A peptide designed from the α5 Helix domain of Cyclin A to competitively inhibit the activity of Cyclin A/CDK2 and/or Cyclin A/Cdc2 (see Brown N R, et al. Structure. 3:1235-47, 1995 and Gondeau C, et al. J Biol Chem 280: 13793-13800, 2005) is shown in relation to several other cyclins (see FIG. 4A). The cytotoxic fragment of Cyclin D2 identified by proteasome screening (see Ferro E S, et al. Journal of Neurochemistry 91: 769-777, 2004 and Araujo C B, et al. J Biol Chem 89: 16711-16726, 2014), and which acts at specific cell cycle phases (see Russo L C, et al. J Proteomics 151: 24-32, 2017), is underlined. With reference to FIG. 4C, the C-terminal (ELAS1) CCNG1 peptide (underlined), which blocks the binding of PP2A to CCNG1 and results in chemosensitization (see Ohno S, et al. Oncogene. December 34: 5983-96, 2015 and Uchihashi T, et al. Oncotarget 8: 85868-85882, 2017), is optimized/lengthened for comparison. The general region of Cyclin G1 responsible for Mdm2 binding is localized to the second tandem repeat (see Zhao L, et al. Mol Cancer Res 1:195-206, 2003); however, the experimental Mdm2-blocking peptides are strategically designed to minimize peptide length and to test the functional requirement of a putative zing-finger motif (CHC sequence).

While cyclin proteins exhibit distinctive structural similarities embodied by the so-called "cyclin-box," a definitive series of alpha-helical segments (alpha-helix 1, 2, 3, 4, and 5) followed by a tandem repeat of helices (alpha-helix 1', 2', 3', 4', and 5'), each type or class of cyclins Cyclin A, B, C, D, E, F, G, H, etc.) functions as an activator and targeting subunit that "targets" its cognate cyclin-dependent protein kinase (CDK) partner to specific substrates at pivotal points in the mammalian cell cycle. This specificity of regulatory function is determined by sequences and structures within these critical cyclin domains. Thus, Cyclin-CDK interactions can be amenable to strategic designs and applications of peptide mimetics that are intended to block the cyclin-dependent functionality of these aberrant players of malignancy (see Zhao L, et al. Mol Cancer Res 1:195-206, 2003 and Eldar-Finkelman H, et al. Current Pharmaceutical Design 15:1-8, 2009).

An aspect of the disclosure is directed to a series of synthetic peptide drugs based on the structure and cytotoxic function of dnG1. Such synthetic peptide drugs can be used in differential diagnosis, prognosis, clinical management of cancers, etc.

Structural homology of human cyclins was aligned with a view of cyclin-derived sequence/substrate-specificity and cell cycle checkpoint function in mind (see FIG. 4A). In contrast to the majority of well-defined CDK inhibitors, ATP antagonist inhibitors described to date, and/or various inhibitors based on CDK phosphorylation sites ( . . . X-S/T-P-X . . . ) found in identified substrate proteins, the individual alpha-5-helix-derived peptides may be highly specific for particular CDKs. Accordingly, the individual alpha-5-helix-derived peptides function by design to provide a stable and competitive alpha-helical structure (i.e., peptide inhibitor) at a critical protein-protein interface that would compete and/or interfere with the assembly, conformation, and/or bioactivity of the respective Cyclin-CDK complexes. Thereby, the individual alpha-5-helix-derived peptides can result in CDK inhibition, cell cycle blockade, and overt cytotoxicity.

FIG. 4B depicts the CCNG1/dnG1 Mdm2-binding domain and two test peptides, with the CPP shown in bold.

It has been reported that Mdm2 binds to the first three a helices of the so-called "box repeat," a C-terminal region of five α-helices (α') containing structural similarity to the cyclin box (see Nilendu P, et al. Current Cancer Therapy Reviews. 13: 1-18, 2017 and Noble M E, et al. Trends Biochem Sci. 22: 482-487, 1997). The C-H-C motif (double underlined) appears reminiscent of a zinc-finger motif.

FIG. 4C depicts the CCNG1/dnG1 PP2A-binding domain. The ELAS1 peptide (underlined) has been reported to sensitize cells to radiation therapy and certain chemotherapies; however, the tiny peptide is much less efficient than wild type CCNG1 in blocking PP2A. Therefore, for the purposes of comparison, peptide mimics are designed as CPP-fusions of similar length.

FIG. 4D shows an "experimental set" of cell cycle blocking peptides (CCBPs) of similar length, designed for direct comparisons, including novel test peptides derived from CyclinG1/dnG1. As indicated, a YGRKKRRQRRR (SEQ ID NO:21) Tat-derived cell penetrating peptide sequence (CPP) is appended to the C-terminus of each test peptide, strategically conjoined without extraneous linkers at the indicated hydrophobic amino acids. In some embodiments, the N-terminus will not be acetylated, nor will the C-terminus be amidated, as this can decrease the solubility of the synthetic peptides. Each peptide will be tested for solubility in water and/or PBS; however, 50% DMSO may be used as needed to prepare a concentrated stock solution.

The elimination of the N-terminal segment of the CCNG1 protein abolishes the sensitivity to ubiquitin-mediated proteolysis, which makes CCNG1 a highly unstable protein (CCNG1's half-life is about 15-20 minutes). However, a further deletion of the defined alpha-helical segments of the CCNG1 "cyclin box" created a highly toxic construct (dnG1) that exhibits broad spectrum bioactivity, including apoptosis (active cell death) in many cancer cells. It was found that: (i) CCNG1 physically targets Cdk5 (and possibly Cdk2) to activate the powerful c-Myc oncoprotein at the initiation (START) of the cell division cycle; and (ii) CCNG1 is an executive component of the pivotal CCNG1/Mdm2/p53 Axis, which determines both DNA fidelity and proliferative cell fate.

The discovery that CCNG1 binds both the PP2A phosphatase and the Mdm2 oncoprotein—resulting in Mdm2 activation and subsequent inhibition/destruction of the p53 tumor suppressor protein—confirms that CCNG1 expression is a major player in the onset and progression of many types of cancers.

Constitutive or deregulated hyperactivity of cyclins due to amplification, overexpression, or mutation of cyclin genes (and/or cognate CDKs) contributes to proliferation of cancer cells, and aberrant activity of these kinases has been reported in a wide variety of human cancers. The set of designer peptide inhibitors provided herein—including the addition of a cell penetrating peptide (CPP) sequence derived from HIV Tat (amino acids 47-57)—can be used to characterize the molecular mechanisms of CCNG1/dnG1 action and to aid in the development and application of specific peptide inhibitors (e.g., dnG1 mimetics) for use in cancer therapy.

Moreover, the defined set of CCNG1-derived peptide inhibitors provided herein, used alone or in combination with other cytotoxic (control) peptides, may find additional utility as companion diagnostics, that is, by providing a functional characterization of biologically active and vulnerable pathways driving cancer cell proliferation. The profile of cyclin-inhibitors may be used to guide treatment options using conventional and/or combinatorial approaches. The CCNG1/dnG1-derived designer peptides may be used to treat cancer. Furthermore, the comprehensive panel of cyclin-derived peptide inhibitors may be employed (for example, in cellulo) as companion diagnostics (e.g., for precision medicine).

CCNG1 is a novel biomarker for cancer. The development of cancer involves a cascade of events that ultimately leads to the acquirement of genetic mutations, which alter the regulation of normal signaling pathways towards uncontrolled cellular proliferation and consequently, tumor formation. Cyclins control the major check points in cell cycle transitions in human cells, and abnormal expression of cyclins has been shown in many human cancers. These include aberrant expression of Cyclins A, B, D, and E in human tumors (see Reimer, C. L., et al. *J Biol Chem*, Vol. 274, No. 16, 11022-9). Among the so-called cyclins, the CCNG1 gene encoding human CCNG1 (see Wu, et al., *Oncol Rep*, Vol. 1, 705-11) is of particular bio-pharmaceutical importance, for it represents the molecular target of DeltaRex-G (formerly named Rexin-G), the first targeted, injectable genetic medicine developed for the treatment and control of a broad spectrum of diverse cancer indications (see Gordon, E. M., et al. *Expert Opin Biol Ther*, Vol. 10, No. 5, 819-32 and Gordon, E. M., et al. Critical stages in the development of the first targeted injectable molecular genetic medicine for cancer. In Chapter 26. Gene Therapy Applications. Intech Publishing, Zagreb, Croatia: 461-462, 2011).

In recent years, the importance of the cyclin CCNG1 proto-oncogene as a new biomarker and prognostic factor for patient outcome has been increasingly evident. In 1994, Wu, et al. reported the molecular cloning of human CCNG1 gene and the overexpression of CCNG1 RNA in osteosarcoma and Ewing's tumor. In 1995, Skotzko, et al. (see *Cancer Res*, Vol. 55, 5493-8) showed that an antisense CCNG1 retroviral vector (G1aG1SvNa) blocked the cell cycle in G1 phase, resulting in apoptosis and inhibition of cell growth of MG-63 osteosarcoma cells. Since then, CCNG1 overexpression in many types of cancer has been reported.

In 2001, Gordon, et al. (see Hum Gene Ther 2001; 12:193-204) showed overexpression of CCNG1 in a subcutaneous human xenograft model of pancreas cancer. Arrest of tumor growth occurred after a seven-day treatment cycle of the DeltaRex-G (formerly Mx-dnG1) vector. Note the intense nuclear immunoreactivity for human CCNG1 protein in the tumor nodule (t) from a control vector-treated animal with minimal staining in the capsule (st) (see FIG. 5, left panel), compared to the markedly reduced immunoreactivity for the human CCNG1 protein in a tumor nodule from the DeltaRex-G vector-treated animal (see FIG. 5, right panel).

Reimer, et al. were the first to describe the potential role of CCNG1 in human breast and prostate cancer. They showed that Cyclin G was overexpressed in breast and prostate cancer cells as well as in cancer cells in situ from tumor specimens, using differential display polymerase chain reaction (PCR) screening. Following DNA damage, Reimer, et al. showed that Cyclin G was triggered to cluster in discrete nuclear DNA replication foci that contain replication-associated proteins such as proliferating cell nuclear antigen (PCNA). The specific subcellular localization of Cyclin G at DNA replication foci provides an additional link between p53-mediated growth arrest and cell cycle regulation and, without being bound by any particular theory, may suggest that Cyclin G acts as an effector of p53-mediated events by functional association with replication foci protein(s).

In 2015, Jiang, et al. (see J Mol Histol. 2015 June; 46:291-302) characterized the clinical significance of CCNG1 and investigated its role in cellular proliferation and apoptosis of epithelial ovarian cancer (EOC). Jiang, et al. found that CCNG1 was up-regulated in EOC tumors compared with normal ovary tissues. CCNG1 expression in EOC was closely correlated with differentiation grade (P=0.009) and malignant tumor cells in ascites (P=0.009). The Kaplan-Meier curve showed that higher expression of CCNG1 was associated with significantly shorter survival in EOC patients. Multivariate analysis suggested CCNG1 expression was an independent prognostic factor for overall survival. Combined immunofluorescence and flow cytometry analysis showed that silencing of CCNG1 with shRNA could promote apoptosis of ovarian cancer cells. In summary, Jiang's, et al. findings suggest that CCNG1 may be involved in the prognosis of EOC patients and be a useful therapeutic target for EOC.

In 2012, Russell, et al. (see Oncogene (2012) 31:2450-2460) demonstrated a novel role for CCNG1. Anti-mitotic chemotherapeutic agents such as taxanes activate the spindle assembly checkpoint (SAC) to arrest anaphase onset, but taxane-exposed cells eventually undergo slippage to exit mitosis. The therapeutic efficacy of taxanes depends on whether slippage after SAC arrest culminates in continued cell survival, or in death by apoptosis. Russell, et al. showed CCNG1 overexpression promoted cell survival after paclitaxel exposure in ovarian cancer cells. Conversely, CCNG1 depletion by RNA interference delayed slippage and enhanced paclitaxel-induced apoptosis. Consistent with these observations, CCNG1 amplification was associated with significantly shorter post-surgical survival in patients with ovarian cancer who had received adjuvant chemotherapy with taxanes and platinum compounds. Collectively, their findings implicate CCNG1 in regulating slippage and the outcome of taxane-induced mitotic arrest, with potential implications for cancer therapy.

In 2003, Perez, et al. (see. *Gastrointest Surg*, Vol. 7, No. 7, 884-9) reported CCNG1 overexpression in 91% of the 90 colorectal tumors. These Cyclin-G1 positive patients were evenly distributed between men and women, and between tumor locations, that is, 36% rectal tumors and 34% right-sided tumors. Thirty-two percent were well differentiated, and 66% were moderately differentiated. Thirty patients (38%) had stage I disease, 16 (20%) had stage II disease, 25 (32%) had stage III disease, and seven (9%) had stage IV disease. The authors concluded that this frequent overexpression of CCNG1 in colorectal carcinogenesis may facilitate new therapeutic approaches directed at downregulating CCNG1 expression or attenuating its oncogenic function in colorectal cancer.

A series of high-throughput screens investigating the role of microRNAs in the pathogenesis of human hepatocellular carcinoma (HCC) identified miR-122 as the preeminent species of microRNA that was either missing or severely down-regulated in approximately 70% of HCC cancers and in all of the HCC-derived cancer cell lines (see Gramantieri, L., et al. *Cancer Res*, Vol. 67, No. 13, 6092-9). These studies identified CCNG1 as a gene target of miR-122, in that there was an inverse correlation between miR-122 and CCNG1 expression that exists in primary liver carcinomas. Loss of miR-122 and associated CCNG1 overexpression was associated not only with increased proliferative potential of HCC cells, but also with disease progression and metastasis (see Coulouarn, et al., 2009. *Oncogene*, Vol. 28, No. 40, 3526-36), while the re-expression of miR-122 was demonstrated to inhibit both the tumorigenic properties (see Bai, et al., 2009. J Biol Chem, Vol. 284, No. 46, 32015-27) and the metastatic potential (see Wen, et al., Hepatology 2012; 55:1787-1798). In terms of molecular-genetic mechanisms of action, it was confirmed that, by modulating CCNG1 expression, miR-122 influenced the stability and the transcriptional activity of p53, as it reduces the metastatic invasiveness of HCC-derived cell lines (see Fornari, et al., 2009. *Cancer Res*, Vol. 69, No. 14, 5761-7). Moreover, the inhibitory effect of experimentally-restored miR-122 expression on CCNG1 levels served to increase the sensitivity of HCC cells to doxorubicin-induced apoptosis, thereby establishing a mechanistic basis for the future development of combined chemotherapy and RNA-based cancer therapies. Taken together with the emerging molecular biology of CCNG1 (see FIG. 5; Gordon, et al., 2011. Critical stages in the development of the first targeted injectable molecular genetic medicine for cancer. In Chapter 26. Gene Therapy Applications. Intech Publishing, Zagreb, Croatia: 461-462, 2011), it becomes clear that the biopharmaceutical agent, DeltaRex-G (a RNA-based genetic medicine that blocks CCNG1 function), essentially restores a natural tumor suppressor function that is inherent in a normally-abundant species of microRNA—a species of microRNA that is lost with the pathogenesis of cancer, particularly that of invasive metastatic cancer.

A qualified immunohistochemical staining assay was used for enumeration of CCNG1 and Ki-67 nuclear staining cells in 17 tissue types across 15 organs (see Table 1). The significance of differences between the number of CCNG1 and Ki-67 nuclear staining cells in normal versus cancerous tissues was evaluated using Student's t-test. Pearson's coefficient of correlation was used to evaluate the relationship between the numbers of Ki-67 versus CCNG1 nuclear stained cells.

The mean CCNG1 nuclear staining percentage for healthy tissues was 2.2%, while that for cancerous tissues was 77.0%. Significant differences were found when comparing CCNG1 nuclear staining percentages between analogous healthy and cancerous tissues (p=0.007475, df=4). The nuclear staining percentages of CCNG1 and Ki-67 share a statistically significant, positive correlation (r=0.889507, p<0.00001). Further, downregulation of CCNG1 expression was noted in a long-term osteosarcoma survivor after CCNG1 inhibitor therapy.

These data indicate that CCNG1 expression is enhanced in cancerous tumors compared to their analogous counterparts and may be useful in predicting a favorable response to CCNG1 inhibitor therapy in patients with solid and hematologic malignancies.

TABLE 1

| Differential Expression of CCNG1 in Tumors | | | |
|---|---|---|---|
| Normal Tissue | CCNG1 Nuclear Staining % | Cancer Cell Line (Tumor) | CCNG1 Nuclear Staining % |
| Breast | 5% | Breast ILC (Tumor) | 20% |
| | | Breast IDC (Tumor) | 35% |
| | | Breast IDC (Tumor) | 95% |
| | | Breast IC (Tumor | 60% |
| | | SK-BR3 Breast Carcinoma | 95% |

TABLE 1-continued

Differential Expression of CCNG1 in Tumors

| Normal Tissue | CCNG1 Nuclear Staining % | Cancer Cell Line (Tumor) | CCNG1 Nuclear Staining % |
|---|---|---|---|
| Liver | 1% | Hepatocellular Carcinoma (Tumor) | 90% |
| | | Hepatocellular Carcinoma (Tumor) | 40% |
| | | Hepatocellular Carcinoma (Tumor) | 5% |
| | | Hepatocellular Carcinoma (Tumor) | 0% |
| Lung | 0% | HCC-78 NSCLC | 90% |
| Brain, Cerebellum | 0% | T98G Glioblastoma | 100% |
| Tongue | 0% | Sarcoma NOS (Tumor) | 70% |
| Skeletal Muscle | 0% | Leiomyosarcoma (Tumor) | 30% |
| | | Angiosarcoma (Tumor) | 90% |
| | | Liposarcoma (Tumor) | 40% |
| | | Chondrosarcoma (Tumor) AD | 0% |
| Colon Epithelium | 30% | Colorectal Carcinoma (Tumor) | 90% |
| | | Colorectal Carcinoma (Tumor) ST | 20% |
| None | | HDLM2 Hodgkins lymphoma | 95% |
| None | | Jurkat T Lymphoblastic Leukemia | 95% |
| None | | Karpas ALL | 100% |
| None | | Jeko-1 Mantle Cell Lymphoma | 95% |
| Prostate | 0% | None | |

The CCNG1 gene encoding human CCNG1 (Wu et al., 1994) is a biomarker of therapeutic importance as CCNG1 represents the molecular target of DeltaRex-G (former names: Mx-dnG1 and Rexin-G) and DeltaRex-GT cell cycle inhibitor gene therapy vectors. Historically, (1) aggregate analysis of clinical data from well-defined Phase I/II and Phase II studies using DeltaRex-G for pancreatic cancer, soft tissue sarcoma, osteosarcoma and breast cancer suggests that DeltaRex-G (encoding the cytocidal dominant negative CCNG1 gene) is safe, and (2) DeltaRex-G as monotherapy improves progression-free and overall survival times in a dose-dependent manner in chemotherapy-resistant sarcoma and pancreatic cancer (see Chawla, S. P., et al. (2009). *Mol Ther*. Vol. 17, 1651-7; Chawla, S. P., et al. (2010). *Mol Ther*. Vol. 18, No. 2, 435-41; Bruckner H, et al., J Clin Oncol 28:15s, 2010 (suppl; abstr 4149); Ganjoo K N, et al. J Clin Oncol 28:15s, 2010 (suppl; abstr 10010); and Chawla S P, et al. Sarcoma Research-International, 3 (1): 1-7 id1024, 2016). Notably, ten patients who were treated with DeltaRex-G after having failed standard therapy are alive nine to eleven years after the start of DeltaRex-G treatment. Since the projected molecular target of DeltaRex-G is CCNG1, which is overexpressed in a number of tumor types, it may be expected that DeltaRex-G will be specifically effective in patients with CCNG1 expressing tumors.

SIG-binding peptides may enhance drug delivery to invading tumors. By sequestering the drugs in the tumor microenvironment, systemic toxicity can be reduced or eliminated. Provided herein are SIG-binding peptides or aptamers that are displayed on the surface of viral vectors. In some embodiments, the SIG-binding sequence is a variation of a cryptic propeptide domain found in von Willebrand factor, which exhibits SIG-binding activity. For example, the SIG-binding sequence can include a minute decapeptide Trp-Arg-Glu-Pro-Ser-Phe-Met-Ala-Leu-Ser (SEQ ID NO:1) or Trp-Arg-Glu-Pro-Gly-Arg-Met-Glu-Leu-Asn (SEQ ID NO:2).

Figure 6:
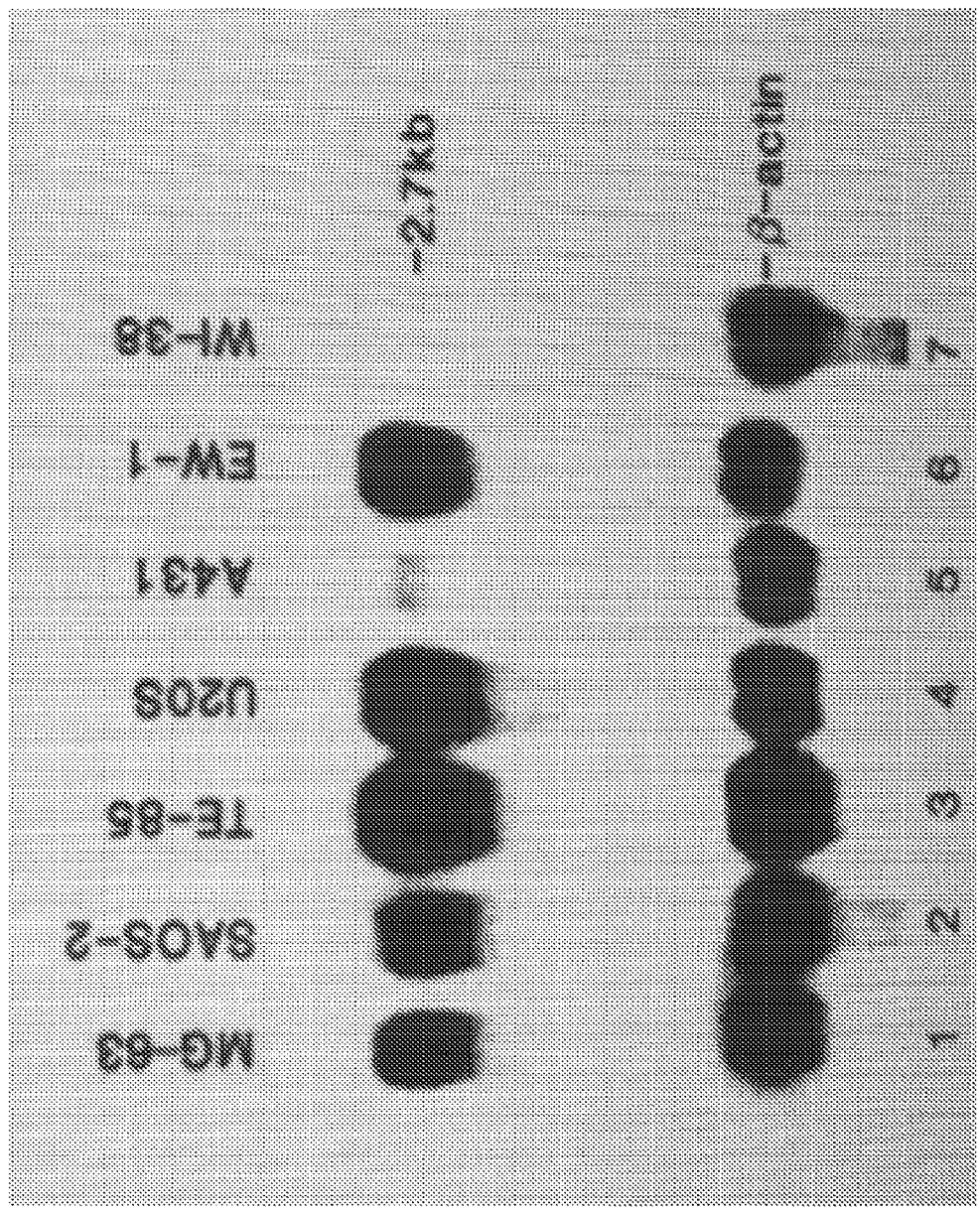
FIG. 6 depicts a northern blot analysis of CCNG1 expression in normal and cancer cells.

FIG. 6 depicts a northern blot analysis of CCNG1 expression in normal and cancer cells. Cytoplasmic RNA isolated from MG-63, SAOS-2, TE-85, and U20S osteosarcoma cells, as well as A431 epithelioid carcinoma, EW-1 Ewing's sarcoma cells, and WI-38 normal diploid fibroblasts, was separated electrophoretically in formaldehyde-agarose gels, transferred to nylon membranes, and hybridized with $^{32}$P-labeled (HS)CFCG/cDNA under high stringency conditions. Cells were harvested during log phase growth. Hybridization to a β-actin probe is shown in the lower panel. Elevated expression is observed in osteosarcoma cells and EW-1 cells, with TE-85, U20S, and EW-1 cells exhibiting the highest levels of expression.

Figure 7:
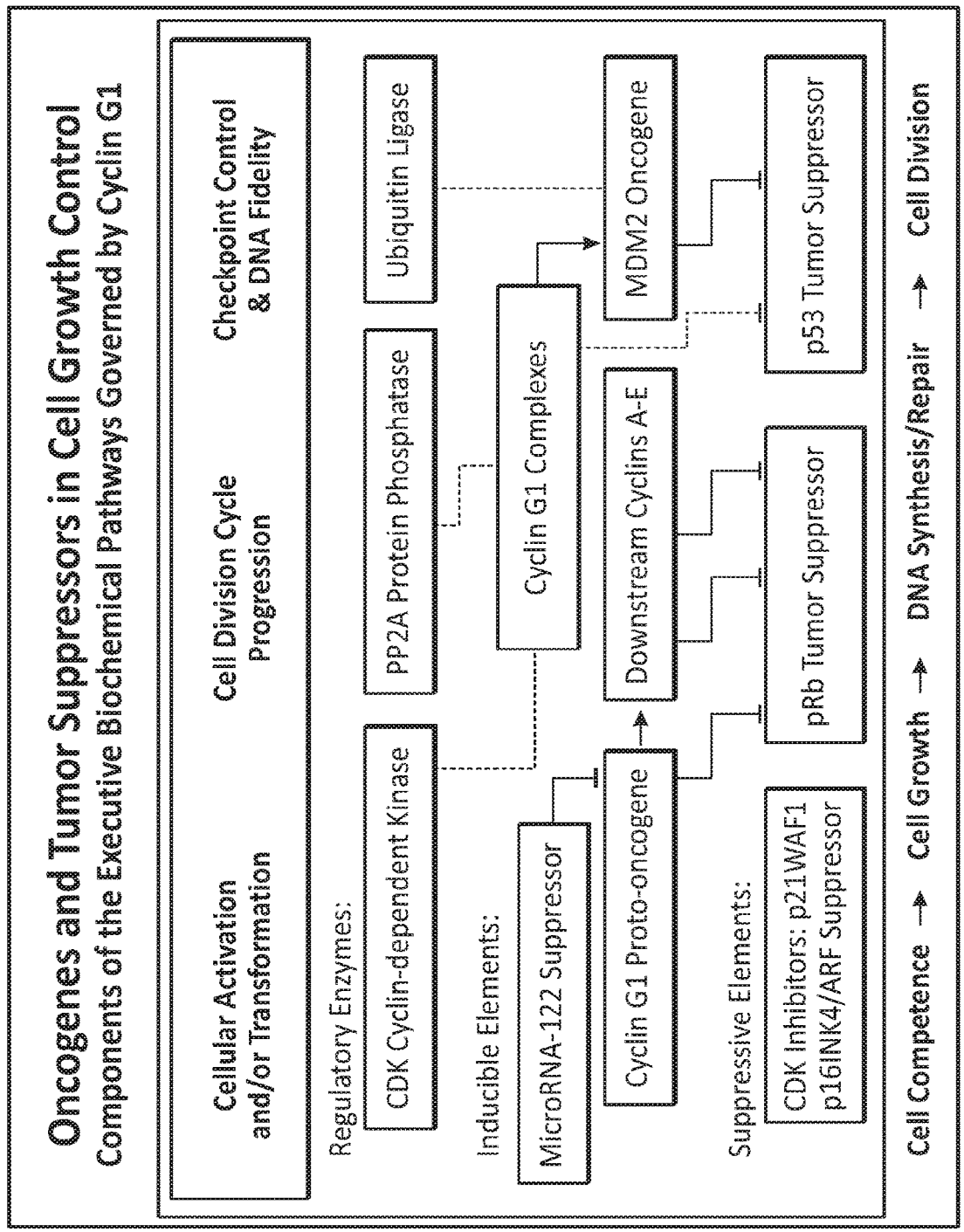
FIG. 7 depicts a diagram of proto-oncogenes and tumor suppressor proteins regulated by CCNG1.

FIG. 7 depicts a diagram of proto-oncogenes and tumor suppressor proteins regulated by CCNG1. As a mitotically-activated (or transformed) cell becomes "competent" to proliferate and passes through the sequential phases of cell growth and DNA synthesis on to cell division, CCNG1 plays a pivotal role in governing the executive enzymatic activities of key regulatory components, including the checkpoints sensing DNA damage and repair. Normally held tightly in check (by microRNA-122), the growth-associated CCNG1 stands at the headwaters of cell cycle progression: advancing the cell cycle (arrows) through a myriad of enzymatic complexes (i) by regulating site-directed protein phosphorylation by cyclin-dependent protein kinases (CDKs), which phosphorylate and inactivate the Rb tumor suppressor protein (blunted arrows), and (ii) by activating the cellular oncoprotein Mdm2, which in turn inactivates the p53 tumor suppressor protein (blunted arrows) by initiating its destruction. CCNG1 governs the enzymatic activities of such key regulatory enzymes by transcriptional control of downstream elements, enzymatic activation/inactivation of the executive enzymes, and by directing the regulatory complexes to specific substrates and/or specific subcellular locations.

One aspect of the present disclosure relates to a method of treating a cancer in a patient. In some embodiments, the method includes obtaining a tumor sample from a patient and detecting whether CCNG1 gene expression is present in the tumor sample. The method can also include diagnosing the patient with a CCNG1 inhibitor-responsive cancer when the presence of CCNG1 gene expression in the tumor sample is detected. Furthermore, the method can include administering an effective amount of a CCNG1 inhibitor to the diagnosed patient.

The tumor sample can be a cancerous tumor sample. In some embodiments, the cancer may be selected from colorectal cancer, breast cancer, ovarian cancer, brain cancer, non-small cell lung cancer, pancreatic cancer, prostate cancer, sarcoma, carcinoma, melanoma, leukemia, lymphoma, and/or a hematologic malignancy. In some other embodiments, the cancer may be selected from another suitable cancer. In various embodiments, the tumor sample may be an archived tumor sample, a biopsied tumor sample, a circulating tumor cell (CTC) sample, or another suitable tumor sample.

Detecting whether CCNG1 gene expression is present in the tumor sample can include determining RNA levels in the tumor sample (e.g., via PCR methods such as reverse transcription followed by quantitative PCT (RT-qPCR), northern blot, use of hybridization arrays, serial analysis of gene expression (SAGE), RNA sequencing (RNA-Seq), next-generation sequencing, fluorescent in situ hybridization (FISH) assay, etc.). In certain embodiments, the method can include detecting whether CCNG1 protein is present in the tumor sample (e.g., via immunohistochemistry, western blot, etc.). For example, the method can include determining whether a "higher" number of cells in the tumor sample express CCNG1 protein. In various embodiments, it can be determined if greater than about 50% of the tumor cells in the tumor sample express CCNG1 protein, greater than about 60% of the tumor cells in the tumor sample express CCNG1 protein, greater than about 70% of the tumor cells in the tumor sample express CCNG1 protein, greater than about 80% of the tumor cells in the tumor sample express CCNG1 protein, greater than about 90% of the tumor cells in the tumor sample express CCNG1 protein, or another suitable percentage of the tumor cells in the tumor sample express CCNG1 protein. In certain embodiments, the CCNG1 protein may be detected using an antibody against the CCNG1 protein. The antibody may be configured for immunohistochemical staining. In other embodiments, the CCNG1 protein may be detected by mass spectrometry. The CCNG1 protein may be a mammalian CCNG1 protein. For example, the CCNG1 protein may be a monkey, a dog, a cat, a horse, a cow, a pig, a goat, a rabbit, a rat, or a mouse CCNG1 protein. The CCNG1 protein may be a human CCNG1 protein.

In some embodiments, the CCNG1 inhibitor-delivering therapeutic may include a binding peptide that is configured to bind one or more signature (SIG) elements of an invading tumor. A vector encoding the CCNG1 inhibitor may also include at least one cytocidal gene. The binding peptide of the CCNG1 inhibitor-delivering therapeutic may include a polypeptide sequence having at least about 80% sequence identity to a polypeptide selected from Trp-Arg-Glu-Pro-Ser-Phe-Met-Ala-Leu-Ser (SEQ ID NO:1) or Trp-Arg-Glu-Pro-Gly-Arg-Met-Glu-Leu-Asn (SEQ ID NO:2). In certain embodiments, the binding peptide may include a polypeptide sequence having at least about 50% sequence identity, at least about 60% sequence identity, at least about 70% sequence identity, at least about 90% sequence identity, or be identical to a polypeptide selected from SEQ ID NO:1 or SEQ ID NO:2.

The binding peptide may be displayed on a surface of a viral vector. Furthermore, the binding peptide may be configured to bind a Gly-Xxx-Pro/Hyp-Ala-Xxx-Pro/Hyp-Gly-Xxx-Pro/Hyp (SEQ ID NO:3) polypeptide sequence that is exposed on a tumor, wherein Xxx is an amino acid other than Gly, Pro, or Hyp. Stated another way, the binding peptide may be configured to bind at least a portion of a polypeptide sequence of collagen.

The gene vector encoding the CCNG1 inhibitor may include at least two cytocidal genes. In some embodiments, the cytocidal gene may be a pro-drug activating system, an HSV-tk gene, an apoptosis-inducing gene, a cyclin-inhibiting gene, and/or another suitable cytocidal gene, including an inhibitory RNA species or antisense construct. The cyclin-inhibiting gene may be a gene whose product acts in a dominant negative way on the product of the cellular cyclin gene. In certain embodiments, the CCNG1 inhibitor may express an angiogenesis modulating gene; a cytokine; a growth factor or immunomodulating gene (e.g., including genes for granulocyte macrophage colony stimulating factor); an interleukin (e.g., interleukin-8); an interferon; a vascular endothelial growth factor (VEGF); an epidermal growth factor (EGF); a hepatocyte growth factor (HGF); a platelet-derived endothelial cell growth factor (PD-ECGF); a platelet-derived growth factor (PDGF); an insulin-like growth factor (IGF); a growth hormone; an angiopoietin; an acidic or a basic fibroblast growth factor (FGF); transforming growth factor, alpha (TGF-alpha); an enzyme; an enzymatic inhibitor; and/or an antibody specific for these growth factors and their receptors.

Furthermore, the CCNG1 inhibitor may include a retrovector encoding a knockout construct of the CCNG1 gene. In various embodiments, the CCNG1 inhibitor may be DeltaRex-G, DeltaRex-GT, a novel cell cycle blocking peptide, or a combination thereof. Other suitable CCNG1 inhibitors, including specific inhibitors of CCNG1 gene expression and/or Cyclin G1 protein functionality, are also within the scope of this disclosure.

In some embodiments, wherein the CCNG1/dnG1-derived peptide inhibitor includes a CCBP (such as, e.g., any one of SEQ ID NOs:22-25 below) conjoined with a defined CPP (e.g., YGRKKRRQRRR (SEQ ID NO:21)) to facilitate intracellular delivery; the construct may include a polypeptide sequence having at least 80% sequence identity to a polypeptide selected from the following: RFTVSDLMRMEKIVLEKVTWK (SEQ ID NO:22), KACHCRIIFSKAKPSVLALSIIA (SEQ ID NO:23), RIIFSKAKPSVLALSIIALEIQA (SEQ ID NO:24), RQLKHSYYRITHLPTIPEMVP (SEQ ID NO:25), or another suitable polypeptide sequence. The Cyclin G1-derived CCBPs may include a polypeptide sequence having at least about 50% sequence identity, at least about 60% sequence identity, at least about 70% sequence identity, at least about 90% sequence identity, or be identical to SEQ ID NO:22, SEQ ID NO:23, SEQ ID NO:24, or SEQ ID NO:25.

Another aspect of the disclosure is directed to a viral vector including a CCNG1 inhibitor as discussed above. For example, the viral vector may include a binding peptide that is configured to bind one or more SIG elements of an invading tumor and at least one cytocidal gene. In various embodiments, the viral vector may be configured to act as a chemosensitizer.

Another aspect of the present disclosure relates to a method of treating a cancer in a patient, wherein the method includes administering to the patient a therapeutically effective amount of a viral vector including a CCNG1 inhibitor as discussed above. The method may further include administering the viral vector prior to administering chemotherapy to the patient (e.g., as a chemosensitizer). In some embodiments, the viral vector may be administered to the patient one time. The viral vector may be administered to the patient two or more times. For example, the viral vector may be administered to the patient three, four, five, six, seven, eight, nine, ten, or another suitable number of times. In certain embodiments, the viral vector may be administered to the patient one or more times per day, one or more times per week, once every other day, or on another suitable dosing schedule. The viral vector may be administered intravenously, intranasally, sublingually, intrarectally, intraperitoneally, intrathoracically, intratumorally, or via another suitable route into the patient.

In various embodiments, the patient may be an animal such as a mammal. The mammal may be a human. Furthermore, the mammal may be selected from a monkey, a dog, a cat, a horse, a cow, a pig, a goat, a rabbit, a rat, or a mouse.

As will be understood by one of ordinary skill in the art, each embodiment disclosed herein can comprise, consist essentially of, or consist of its particular stated element, step, ingredient, or component. As used herein, the transition term "comprise" or "comprises" includes, but is not limited to, the stated elements, steps, ingredients, or components and allows for the inclusion of unspecified elements, steps, ingredients, or components, even in major amounts. The transitional phrase "consisting of" excludes any element, step, ingredient, or component not specified. The transition phrase "consisting essentially of" limits the scope of the embodiment to the specified elements, steps, ingredients, or components, and to those that do not materially affect the embodiment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e., denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in its respective testing measurements.

The terms "a," "an," and "the," and similar referents used in the context of describing the disclosure (especially in the context of the following claims), are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples or exemplary language (e.g., "such as") provided herein is intended merely to better illuminate the disclosure and does not pose a limitation on the scope of the disclosure otherwise claimed. No language in the specification should be construed as indicating that any non-claimed element is essential to the practice of the disclosure.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

EXAMPLES

The following examples are illustrative of disclosed methods and compositions. In light of this disclosure, those of skill in the art will recognize that variations of these examples and other examples of the disclosed methods and compositions would be possible without undue experimentation.

Example 1—Validation of a Companion Diagnostic Assay for DeltaRex-G

A companion diagnostic assay can include an immunohistochemical staining assay (or qualified immunohistochemical staining assay), which is used to quantify the number of tumor cells expressing CCNG1 protein in resected or biopsied tumors or circulating tumor cells. The response of patients treated with DeltaRex-G having tumors expressing CCNG1 versus patients treated with DeltaRex-G having tumors not expressing CCNG1 can be compared.

Additionally, the response of patients treated with DeltaRex-G having tumors with a "higher" number of cells expressing CCNG1 (e.g., >50% of the tumor cells express CCNG1) versus patients treated with DeltaRex-G having tumors with a "lower" number of cells expressing CCNG1 (e.g., <50% of the tumor cells express CCNG1) can be compared.

The companion diagnostic assay can be validated by determining if CCNG1 expression is essential and/or useful in predicting a patient's tumor response to DeltaRex-G, i.e., the higher the CCNG1 expression in tumors, the greater the tumor response to DeltaRex-G. A companion diagnostic assay may also be an assay for gene expression (e.g., by RNA sequencing or based on a fluorescent in situ hybridization (FISH) assay).

Example 2—Validation of a Companion Diagnostic Assay for a Cell Penetrating Peptide A companion diagnostic assay can include an immunohistochemical staining assay (or qualified immunohistochemical staining assay), which is used to quantify the number of tumor cells expressing CCNG1 protein in resected or biopsied tumors or circulating tumor cells. The response of patients treated with a cell penetrating peptide having tumors expressing CCNG1 versus patients treated with cell penetrating peptide having tumors not expressing CCNG1 can be compared.

Additionally, the response of patients treated with the cell penetrating peptide having tumors with a higher number or percentage of cells expressing CCNG1 (e.g., >50% of the tumor cells express CCNG1) versus patients treated with the cell penetrating peptide having tumors with a lower number or percentage of cells expressing CCNG1 (e.g., <50% of the tumor cells express CCNG1) can be compared.

The companion diagnostic assay can be validated by determining if CCNG1 expression is essential and/or useful in predicting a patient's tumor response to the cell penetrating peptide, i.e., the higher the CCNG1 expression in tumors, the greater the tumor response to the cell penetrating peptide.

Example 3—Use of CTCs in Companion Diagnostic Assays

As noted in Examples 1 and 2, companion diagnostic assays may also be applied to circulating tumor cells (CTCs). CTCs may be isolated by their larger size and rigidity as compared to other cells in the bloodstream. Furthermore, the CTCs can be confirmed by using a fluorescent antibody or peptide, which is directed at vimentin or collagen. CTCs may also be isolated by direct fluorescent antibody staining using a liquid biopsy system.

Certain embodiments of this disclosure are described herein, including the best mode known to the inventors for carrying out the disclosure. Of course, variations on these described embodiments will become apparent to those of ordinary skill in the art upon reading the foregoing description. The applicants expect skilled artisans to employ such variations as appropriate, and the applicants intend for the various embodiments of the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, numerous references have been made to patents and printed publications throughout this specification. Each of the above-cited references and printed publications are individually incorporated herein by reference in their entirety.

It is to be understood that the embodiments of the present disclosure are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The particulars shown herein are by way of example and for purposes of illustrative discussion of the preferred embodiments of the present disclosure only and are presented in the cause of providing what is believed to be the most useful and readily understood description of the principles and conceptual aspects of various embodiments of the disclosure.

It will be apparent to those having skill in the art that many changes may be made to the details of the above-described embodiments without departing from the underlying principles of the disclosure. The scope of the present invention should, therefore, be determined only by the following claims.

The invention claimed is:

1. A therapeutic comprising a viral vector encoding an inhibitor of cyclin G1 activity and at least one cytocidal gene selected from the group consisting of a gene encoding a pro-drug activating system, a herpes simplex virus thymidine kinase (HSV-tk) gene, an apoptosis-inducing gene, a gene encoding an inhibitory RNA, and a gene encoding an antisense RNA, wherein the viral vector displays a signature (SIG) element binding peptide on its surface, wherein the SIG element binding peptide binds a Gly-Xxx-Pro/Hyp-Ala-Xxx-Pro/Hyp (SEQ ID NO: 3) polypeptide.

2. The therapeutic of claim 1, wherein the SIG element binding peptide comprises an amino acid sequence selected from SEQ ID NO:1 or SEQ ID NO: 2.

3. The therapeutic of claim 1, wherein the SIG element binding peptide comprises SEQ ID NO:1 or SEQ ID NO:2.

4. The therapeutic of claim 1, wherein the inhibitor of cyclin G1 activity is selected from the group consisting of a dominant negative Cyclin G1 (CCNG1) mutant construct and a polypeptide consisting of SEQ ID NO:22, SEQ ID NO:23, SEQ ID NO:24, or SEQ ID NO:25.

5. The therapeutic of claim 1, wherein the viral vector is a murine leukemia virus (MLV)-based vector.

6. A method of treating a cancer that expresses CCNG1 in an individual, comprising administering to the individual a therapeutic comprising a viral vector encoding at least two cytocidal genes comprising an inhibitor of cyclin G1 activity and a herpes simplex virus thymidine kinase (HSV-tk) gene.

7. The method of claim 6, wherein the viral vector displays a signature (SIG) element binding peptide on its surface.

8. The method of claim 7, wherein the SIG element binding peptide binds a Gly-Xxx-Pro/Hyp-Ala-Xxx-Pro/Hyp (SEQ ID NO:3) polypeptide.

9. The method of claim 7, wherein the SIG element binding peptide comprises an amino acid sequence selected from SEQ ID NO: 1 or SEQ ID NO: 2.

10. The method of claim 7, wherein the SIG element binding peptide comprises SEQ ID NO:1 or SEQ ID NO:2.

11. The method of claim 6, wherein the inhibitor of cyclin G1 activity is selected from the group consisting of a dominant negative Cyclin G1 (CCNG1) mutant construct and a polypeptide consisting of SEQ ID NO:22, SEQ ID NO:23, SEQ ID NO:24, or SEQ ID NO: 25.

12. The method of claim 6, wherein the viral vector is an MLV-based vector.

* * * * *